US012721663B2

(12) United States Patent
Singh et al.

(10) Patent No.: US 12,721,663 B2
(45) Date of Patent: Sep. 1, 2026

(54) LOCKING SYSTEM FOR FEMORAL NECK FRACTURE FIXATION

(71) Applicant: Stryker European Operations Limited, Carrigtwohill (IE)

(72) Inventors: Jetinder Singh, Gurgaon (IN); Venkateswaran Perumal, Gurgaon (IN); Harpreet Singh, New Delhi (IN); Diksha Babhoota, Gurgaon (IN); Abhishek Kulkarni, Mumbai (IN)

(73) Assignee: Stryker European Operations Limited, Carrigtwohill (IE)

( * ) Notice: Subject to any disclaimer, the term of this patent is extended or adjusted under 35 U.S.C. 154(b) by 156 days.

(21) Appl. No.: 18/440,224

(22) Filed: Feb. 13, 2024

(65) Prior Publication Data

US 2024/0180598 A1 Jun. 6, 2024

Related U.S. Application Data

(63) Continuation of application No. 16/826,967, filed on Mar. 23, 2020, now Pat. No. 11,918,261.

(60) Provisional application No. 62/833,112, filed on Apr. 12, 2019.

(51) Int. Cl.

| | |
|---|---|
| ***A61B 17/84*** | (2006.01) |
| ***A61B 17/80*** | (2006.01) |
| ***A61B 17/86*** | (2006.01) |
| *A61B 17/68* | (2006.01) |

(52) U.S. Cl.

CPC ...... *A61B 17/8057* (2013.01); *A61B 17/8635* (2013.01); *A61B 2017/681* (2013.01)

(58) Field of Classification Search

CPC ................. A61B 17/844; A61B 17/86–17/869

See application file for complete search history.

(56) References Cited

U.S. PATENT DOCUMENTS

| | | | |
|---|---|---|---|
| 3,002,514 A | 10/1961 | Deyerle | |
| 3,678,925 A | 7/1972 | Fischer et al. | |
| 4,519,100 A | 5/1985 | Wills et al. | |
| 5,429,641 A | 7/1995 | Gotfried | |
| 5,759,184 A | 6/1998 | Santangelo | |
| 5,976,139 A * | 11/1999 | Bramlet | A61B 17/8004 606/907 |

(Continued)

FOREIGN PATENT DOCUMENTS

| | | |
|---|---|---|
| GB | 1276147 A | 6/1972 |
| JP | H08112290 A | 5/1996 |

(Continued)

*Primary Examiner* — Zade Coley

(74) *Attorney, Agent, or Firm* — Lerner David LLP

(57) ABSTRACT

A fixation device for providing rotation stability to a femoral neck fracture. The device includes a bone plate having at least one opening, a compression screw housing extendable through the opening of the bone plate, a compression screw being at least partially disposed within the bore of the housing and selectively moveable through the bore, and a collapsible and expandable anchoring member coupled to the compression screw. The anchoring member is configured to transition between a collapsed condition and an expanded condition upon advancement of the anchoring member from the compression screw housing to rotationally stabilize the compression screw within a femur.

15 Claims, 18 Drawing Sheets

(56) References Cited

U.S. PATENT DOCUMENTS

| | | | | |
|---|---|---|---|---|
| 6,783,530 | B1 | 8/2004 | Levy | |
| 7,488,320 | B2 * | 2/2009 | Middleton | A61B 17/746 606/92 |
| 9,452,003 | B2 | 9/2016 | Voor | |
| 9,622,872 | B2 | 4/2017 | McKay | |
| 9,724,141 | B2 | 8/2017 | Thornes | |
| 9,820,785 | B2 | 11/2017 | Benedict | |
| 11,109,897 | B2 | 9/2021 | Suddaby | |
| 2002/0165544 | A1 | 11/2002 | Perren et al. | |
| 2004/0193162 | A1 | 9/2004 | Bramlet et al. | |
| 2005/0166724 | A1 * | 8/2005 | Castaneda | B25B 15/008 81/436 |
| 2008/0161805 | A1 * | 7/2008 | Saravia | A61B 17/7266 606/60 |
| 2008/0177334 | A1 * | 7/2008 | Stinnette | A61B 17/8028 606/301 |
| 2008/0262497 | A1 | 10/2008 | Nijenbanning et al. | |
| 2010/0023012 | A1 | 1/2010 | Voor | |
| 2010/0145396 | A1 | 6/2010 | Thornes | |
| 2010/0222827 | A1 * | 9/2010 | Griffiths | A61B 17/8877 606/104 |
| 2011/0319946 | A1 * | 12/2011 | Levy | A61B 17/8685 606/300 |
| 2012/0010668 | A1 * | 1/2012 | Shimko | A61B 17/8685 606/313 |
| 2012/0172934 | A1 * | 7/2012 | Fisher | A61B 17/8858 606/92 |
| 2014/0025125 | A1 * | 1/2014 | Sack | A61B 17/8625 606/232 |
| 2017/0143387 | A1 | 5/2017 | Jansen | |

FOREIGN PATENT DOCUMENTS

| | | | |
|---|---|---|---|
| JP | 3195666 | U | 1/2015 |
| WO | 2005094705 | A2 | 10/2005 |

* cited by examiner

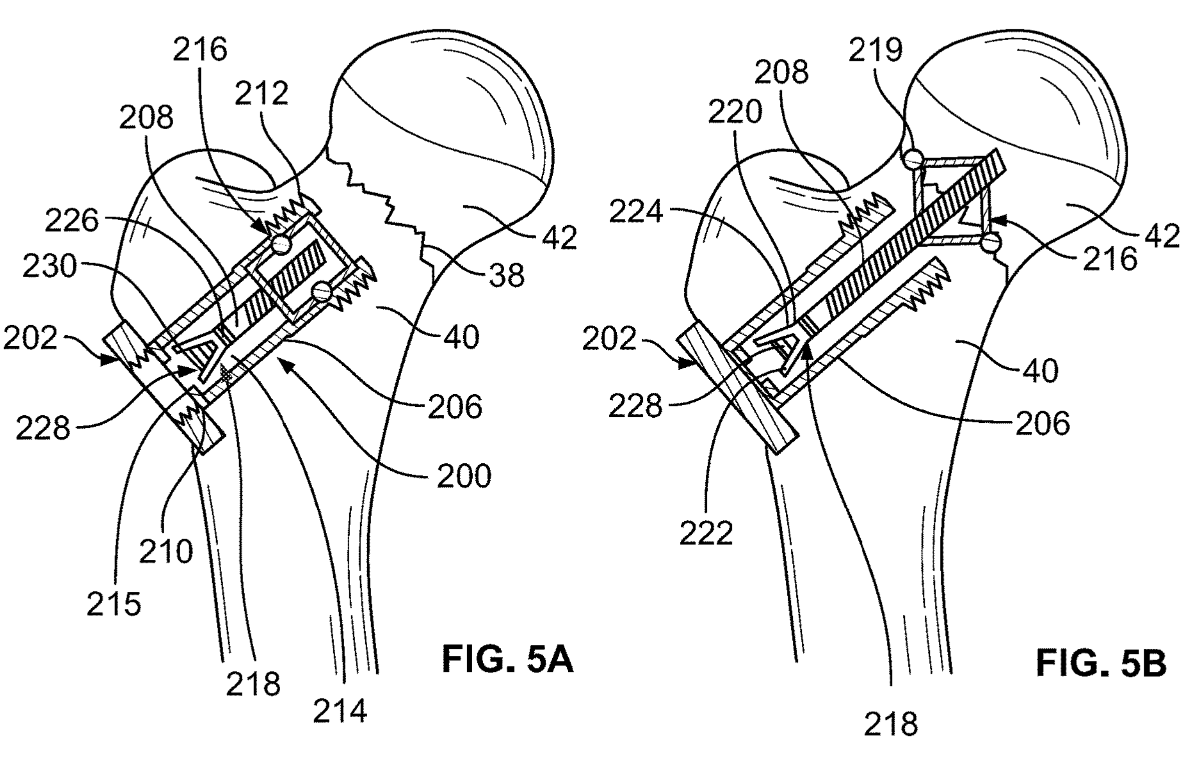
216
212
208
226
230
202
228
210
215
218
214
42
38
40
206
200
219
220
224
216
202
228
222
218
FIG. 5A
FIG. 5B
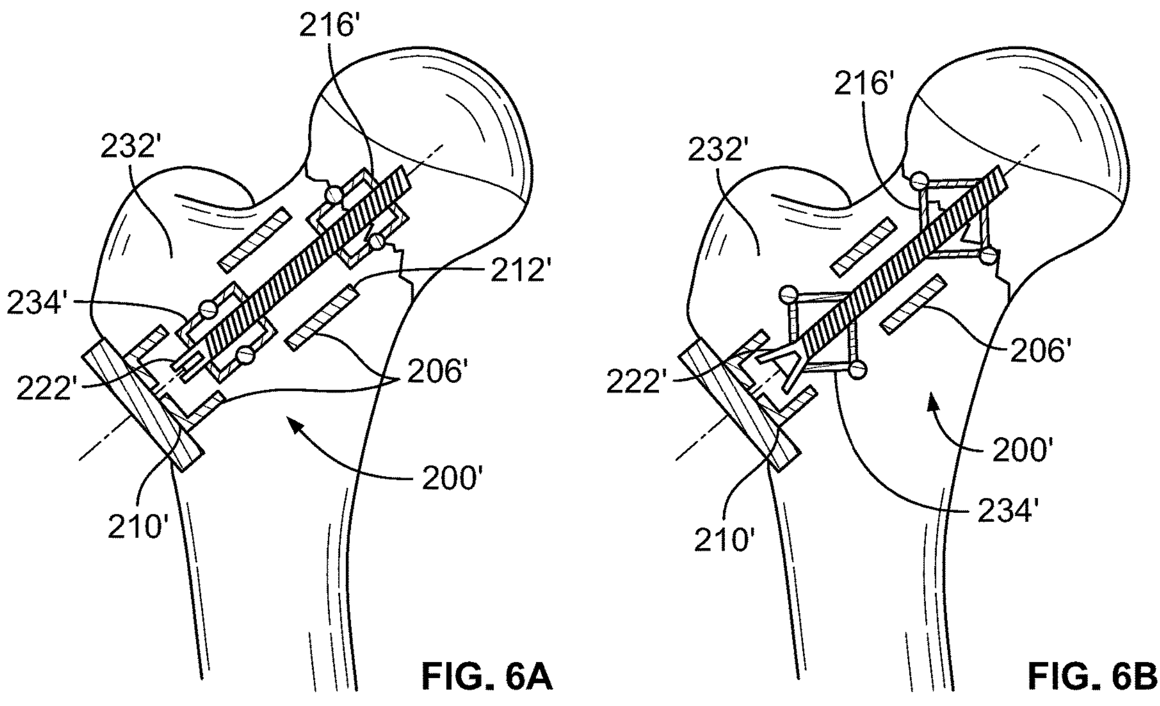
216'
232'
234'
222'
210'
212'
206'
200'
FIG. 6A
FIG. 6B 316
334
306
308
300

316
334
306
308
300

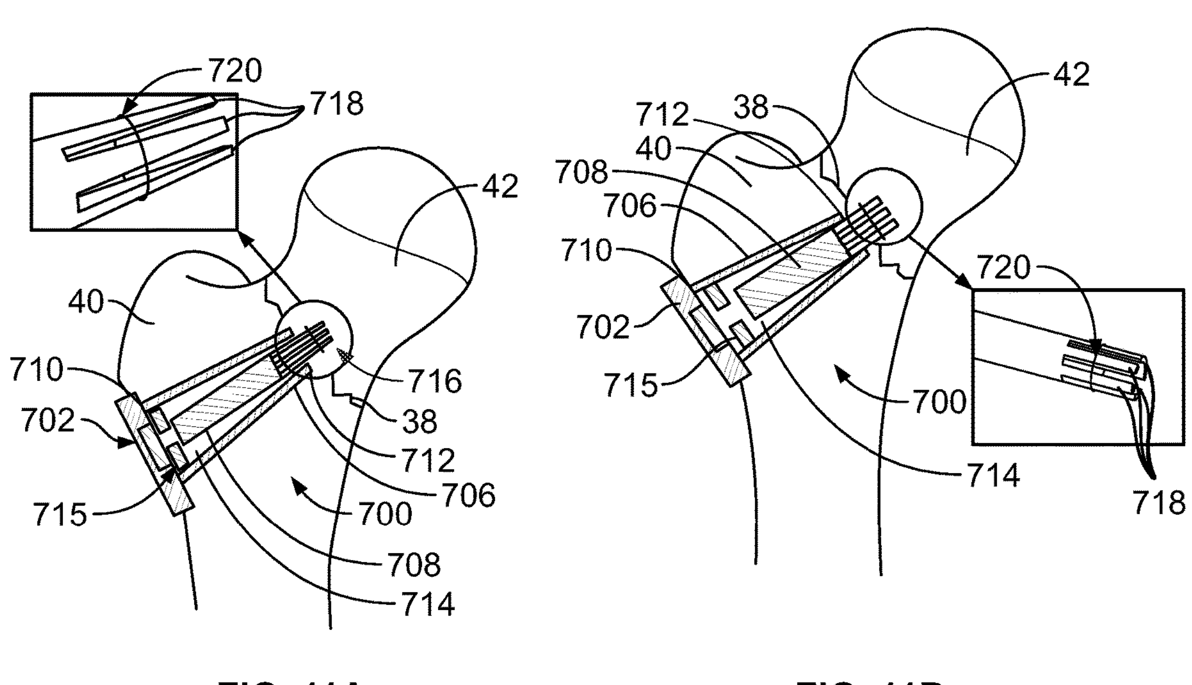
FIG. 11A
FIG. 11B
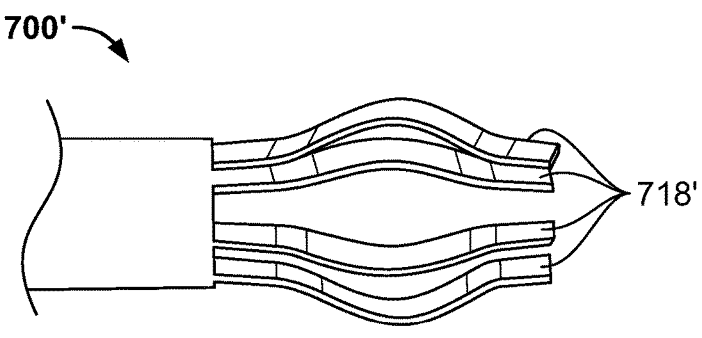
FIG. 11C
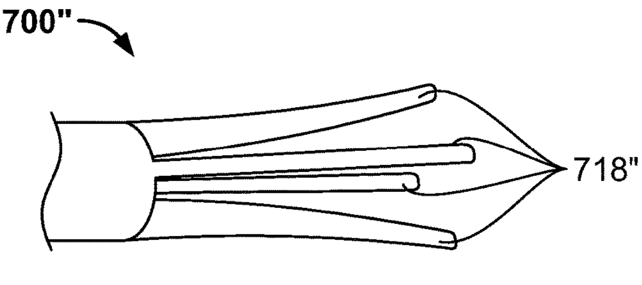
FIG. 11D

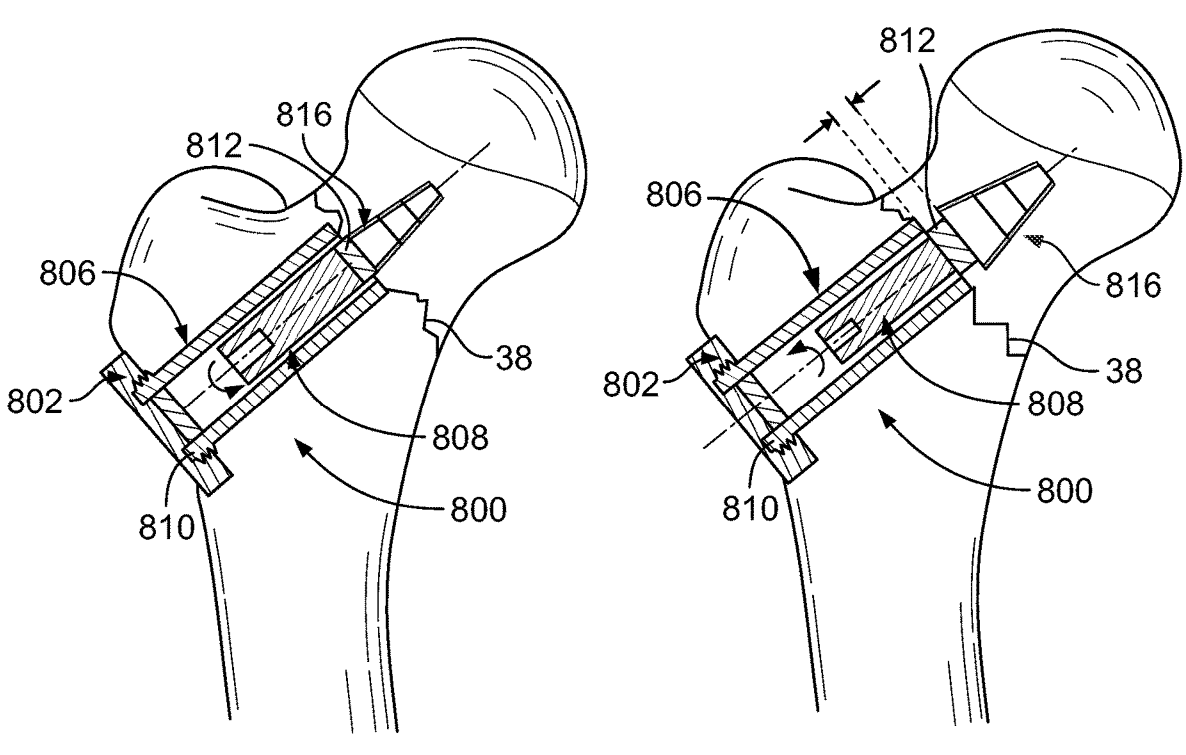
FIG. 12A
FIG. 12B
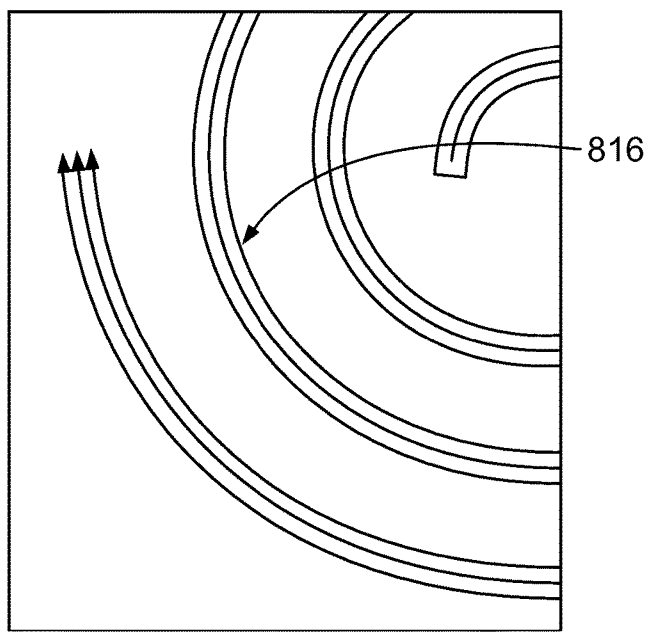
FIG. 12C 812
816
808
806
810
800

812
816
808
806
810
800

LOCKING SYSTEM FOR FEMORAL NECK FRACTURE FIXATION

CROSS-REFERENCE TO RELATED APPLICATIONS

This application is a continuation of U.S. application Ser. No. 16/826,967, filed on Mar. 23, 2020, which claims the benefit of the filing date of U.S. Provisional Patent Application No. 62/833,112 filed Apr. 12, 2019, the disclosures of which are hereby incorporated herein by reference.

BACKGROUND OF THE INVENTION

The present invention relates generally to an apparatus for the treatment of fractures of long bones, for example, fractures of the proximal femur including the neck of the femur and the intertrochantric region.

Femoral neck fractures are often treated with fixation devices, such as intramedullary nails or bone plates that affix the fractured bone portions together and provide stability to the bone during osteogenesis. Postoperative movement of the bone fragments can lead to complications such as shortening of the neck of the femur, which may result in reduced physical function. It is therefore desirable to compress the fracture site intra-operatively and then stabilize the bone portions to minimize their postoperative movement during healing of the bone.

In the case of intramedullary nails, a surgeon inserts a nail into the intramedullary canal of a patient and then inserts a lag screw or barrel through the intramedullary nail and into the neck of the femur to prevent relative movement of the fractured bone portions. Bone plates on the other hand, are placed on an external surface of the femur adjacent the site of the fracture and secured to the femur by a plurality of screws that are inserted through the bone plate.

Traditional intramedullary nails and bone plating systems are not without drawbacks. For example, screws of a conventional bone plating systems have threads on the head portion in addition to threads on the shaft. The threads on the head portion have a greater core diameter than the threads on the shaft. Thus, when the screw is advanced into the bone and the head of the screw is positioned within the screw hole of the bone plate, the threads on the screw head engage corresponding threads in the screw hole and lock the screw in place. This engagement prevents the screw from backing out of the bone plate. Because axial advancement of the conventional screws is limited by the threads on the head of the screw, these systems are often insufficient in compressing the fracture site. Other bone plating systems utilize compression screws which have threadless heads such that the head of the compression screw may be advanced beyond the bone plate to sufficiently collapse the fracture site. When compression screws are used, however, it is often necessary to place an endcap into the compression screw hole of the bone plate to prevent the screw from backing out of the bone plate.

Furthermore, traditional intramedullary nails and bone plating systems are often insufficient in providing rotational stability to the fractured bone portions. Angular rotation of fractured bone portions may cause severe pain and lead to complications including non-union of the bone and avascular necrosis.

Therefore, there is a need for easy to use bone plating systems that provide intra-operative compression and post-operative axial and angular stability to the fractured bone portions.

BRIEF SUMMARY OF THE INVENTION

In accordance with a first aspect of the present invention, a fracture fixation device is provided. The device includes a bone plate having at least one opening and a bone facing surface shaped to engage a proximal femur, a compression screw housing and a compression screw. The compression screw housing is extendable through the opening of the bone plate and includes an engagement feature at a proximal end of the housing that is adapted to engage with the opening of the bone plate to secure the compression screw housing to the bone plate. The compression screw housing defines a bore extending between the proximal and distal ends for receiving the compression screw. The compression screw is insertable within the bore of the housing and selectively moveable through the bore. The compression screw includes a first collapsible and expandable anchoring member that is configured to transition between a collapsed condition in which the anchoring member has a first diameter in a radial direction and an expanded condition in which the anchoring member has a second diameter in the radial direction, the second diameter being greater than the first diameter. Distal advancement of the anchoring member from the bore of the compression screw housing causes the anchoring member to automatically transition from the collapsed condition to the expanded condition and assists in axially and rotationally securing the compression screw to bone.

In accordance with another aspect of the invention, a fracture fixation device includes a bone plate having at least one opening and a bone facing surface shaped to engage a proximal femur, a compression screw housing and an anchoring member. The compression screw housing is adapted to extend through the opening of the bone plate and includes a proximal end having an engagement feature that is adapted to engage with the bone plate. The compression screw housing defines a bore extending between the proximal end and a distal end for receiving the compression screw. The compression screw is at least partially insertable within the bore of the housing and includes a plurality of fingers formed from a shape memory material capable of transitioning between a collapsed condition and an expanded condition to assist in axially and rotationally securing the compression screw relative to the femur.

In yet another aspect of the invention, a fracture fixation device includes a bone plate having at least one threaded opening and a bone facing surface shaped to engage a proximal femur, a barrel extendable through the opening of the bone plate, a lag screw and a lead screw. The barrel may define a bore extending between a proximal end and a distal end of the barrel. The proximal end of the barrel may include an external thread adapted to engage the at least one threaded opening of the bone plate. The lag screw includes a proximal end, a distal end and a bore extending between the proximal and distal ends of the lag screw. The lag screw is at least partially insertable within the barrel and includes an external thread for engaging bone, an internal thread disposed adjacent the proximal end of the lag screw, an internal thread disposed adjacent the distal end of the lag screw, and a plurality of pivotal arms attached to the distal end of the lag screw and transitionable between a first condition in which the arm members extend parallel to a longitudinal axis of the lag screw and a second condition in which the arm members extend radially outward from the longitudinal axis of the lag screw. The lead screw is at least partially disposed within the bore of the lag screw and selectively moveable therethrough. The fixation device further includes a proximal wedge having an external thread cooperatively engaged with the internal thread adjacent the proximal end of the lag screw, and a distal wedge having an external thread cooperatively engaged with the internal thread adjacent the distal end of the lag screw. The proximal and distal wedges are coupled to the lead screw such that rotation of the proximal wedge axially advances the lead screw causing the distal wedge to contact the arm members to transition the arm members from the first condition to the second condition.

In accordance with another aspect of the invention, a fixation device for stabilizing fractured bone comprises a bone plate having at least one opening, a housing having a proximal end adapted to be secured to the bone plate, a distal end opposite the proximal end and a bore extending between the proximal and distal ends, the housing defining a longitudinal axis, a compression screw being at least partially disposed within the bore of the housing and selectively moveable through the bore, and a first anchoring member coupled to the compression screw and configured to transition between a first condition in which a portion of the first anchoring member has a first distance from the longitudinal axis and a second condition in which the portion of the first anchoring member has a second distance from the longitudinal axis, the second distance being greater than the first distance, wherein the portion of the first anchoring member transitions from the first condition to the second condition to allow the portion of the first anchoring member to engage bone and assist in axially and rotationally securing the fractured bone portions. The housing may be a lag screw having an external thread provided adjacent the proximal end, the external thread being configured to be selectively secured to a corresponding thread disposed within the at least opening of the bone plate to lock the lag screw to the bone plate. The anchoring member may comprise a plurality of prongs biased radially outward with respect to a longitudinal axis of the compression screw. A proximal end of the compression screw may include a plurality of pivotal leg members transitionable between a first condition in which each of the leg members extends parallel to a longitudinal axis of the compression screw and a second condition in which each of the plurality of pivotal leg members extends outwardly with respect to the longitudinal axis of the compression screw and prevents the compression screw from backing out of the housing. The plurality of pivotal leg members may define an interior surface having an internal thread. The device may further comprise a conical wedge including an external thread corresponding to the internal thread of the leg members such that rotation of the conical wedge in a first direction advances the conical wedge toward the compression screw, and wherein engagement of the conical wedge with the plurality of legs causes the legs to transition to the second condition. The housing may be a barrel having a sidewall defining a first slot axially located between the proximal end and the distal end of the barrel. The portion of the first anchoring member may be sized and configured to extend through the first slot when transitioning from the first condition to the second condition. The compression screw may define a second slot axially located between the proximal end and the distal end of the barrel. The device of claim may further comprise a second anchoring member coupled to the compression screw, a portion of the second anchoring member being sized and configured to extend through the second slot when the second anchoring member is positioned radially adjacent the second slot. The second slot may be proximal to the first slot, and the second anchoring member is proximal to the first anchoring member. The second slot may be circumferentially distanced from the first slot, and the second anchoring member is circumferentially distanced from the first anchoring member. A first end of the first anchoring member may be coupled to a first connector and a second end of the first member is coupled to a second connector, wherein transitioning from the first condition to the second condition includes the first connector axially moving relative to the second connector. The anchoring member may include a wound spiral tip having a base with a diameter in the second condition that is larger than a diameter of the bore of the housing. The wound spiral tip may form a substantially frustoconical shape in the second condition. The wound spiral tip may be wound about a distal end of the compression screw. The compression screw may include a sidewall defining a plurality of outwardly arching tracks extending from the bore of the housing through an external surface of the compression screw. The compression screw may include a plurality of outwardly biased fingers extending from a distal end of the compression screw and configured extend through the outwardly arching tracks as the compression screw is distally advanced. A first finger of the plurality of outwardly biased fingers may be at least one of a circumferential and axial distance away from a second finger of the plurality of outwardly biased fingers. The compression screw may be cannulated and configured to receive a k-wire. The device may further comprise a k-wire extendable through the compression screw. The anchoring member may transition from the first condition to the second condition by axially moving a second portion of the anchoring member.

In accordance with another aspect, a fixation device for stabilizing fractured bone comprises a bone plate having at least one opening, a housing having a proximal end adapted to engage with the bone plate, a distal end opposite the proximal end and a bore extending between the proximal and distal ends, a pin at least partially disposed within the bore of the housing, the pin including a plurality of fingers formed from a shape memory material capable of transitioning between a first condition in which the plurality of fingers extend inwardly toward a longitudinal axis of the pin such that the fingers may be inserted through the distal end of the housing and a second condition in which a portion of the plurality of fingers radially expand to assist in axially and rotationally securing the fractured bone portions. The shape memory material may comprise nitinol. The plurality of fingers may include four fingers equidistantly spaced 90 degrees from one another about a circumferential edge of the compression screw. A gap may be defined between adjacent fingers. The device may further comprise a circlip disposed about the plurality of fingers and adapted to control the expansion of the fingers. In the second condition, only the intermediate portion of the plurality of fingers may radially expand.

In accordance with another aspect, a fixation device for stabilizing fractured bone comprises a bone plate having at least one opening, a barrel extendable through the opening of the bone plate, the barrel having a proximal end with an external thread adapted to engage the at least one threaded opening of the bone plate, a distal end opposite the proximal end and a bore extending between the proximal and distal ends, a lag screw being at least partially disposed within the barrel and having a proximal end, a distal end and a bore extending between the proximal and distal ends, the lag screw including an external thread adapted to engage bone, an internal thread disposed adjacent the proximal end of the lag screw, and a plurality of arms attached to the distal end of the lag screw and transitionable between a first condition in which the arm members extend parallel to a longitudinal axis of the lag screw and a second condition in which the arm members extend radially outward from the longitudinal axis of the lag screw, a lead screw disposed within the bore of the lag screw and selectively moveable through the bore of the lag screw, a distal wedge having an external thread cooperatively engaged with the internal thread adjacent the distal end of the lag screw, wherein the distal wedge is coupled to the lead screw and movement of the lead screw axially moves the distal wedge such that the distal wedge contacts the plurality of arm members to transition the arm members from the first condition to the second condition. The lag screw may have an internal thread disposed adjacent the distal end of the lag screw, and the fixation device further comprises a proximal wedge having an external thread cooperatively engaged with the internal thread adjacent the proximal end of the lag screw. Rotation of the proximal wedge may axially advance the lead screw such that the distal wedge contacts the plurality of arm members to transition the arm members from the first condition to the second condition.

BRIEF DESCRIPTION OF THE DRAWINGS

FIG. 5A is a schematic representation of a fracture fixation device mounted on a proximal femur having a radially expandable anchor in a collapsed condition according to one aspect of the present disclosure.

FIG. 5B is a schematic representation of the fracture fixation device of FIG. 5A showing the radially expandable anchor in the expanded condition.

FIG. 6A is a schematic representation of a variant fracture fixation device mounted on a proximal femur having a radially expandable anchor in a collapsed condition according to another aspect of the present disclosure.

FIG. 6B is a schematic representation of the fracture fixation device of FIG. 6A showing the radially expandable anchor in the expanded condition.

FIG. 11A is a schematic representation of a fracture fixation device mounted on a proximal femur having a radially expandable anchor in a collapsed condition according to another aspect of the present disclosure.

FIG. 11B is a schematic representation of the fracture fixation device of FIG. 11A showing the radially expandable anchor in the expanded condition.

FIG. 11C is a partial view of a fracture fixation device according to another aspect of the present disclosure.

FIG. 11D is a partial view of a fracture fixation device according to another aspect of the present disclosure.

FIG. 12A is a schematic representation of a fracture fixation device mounted on a proximal femur having a radially expandable tip in a collapsed condition according to another aspect of the present disclosure.

FIG. 12B is a schematic representation of the fracture fixation device of FIG. 12A showing the radially expandable tip in the expanded condition.

FIG. 12C is a schematic front elevation view of the radially expandable tip of the fracture fixation device of FIG. 12A.

DETAILED DESCRIPTION

As used herein, when referring to the femur or other parts of the body, the term “proximal” means closer to the heart and the term “distal” means more distant from the heart. The term “inferior” means toward the feet of a patient and the term “superior” means towards the head of the patient. The term “anterior” means towards the front part of the body or the face and the term “posterior” means towards the back of the body. The term “medial” means toward the midline of the body and the term “lateral” means away from the midline of the body. When referring to the compression screw housing or the compression screw or pin, the term "proximal" means closer to the user, wherein as the term "distal" means further from the user.

Throughout this description, a fracture refers to femoral neck fracture, however, the devices and methods described hereinafter can be used to fixate fractures in any long bone, for example, a tibia or a humorous, whether the fracture be naturally occurring or surgeon-induced.

Figure 1:
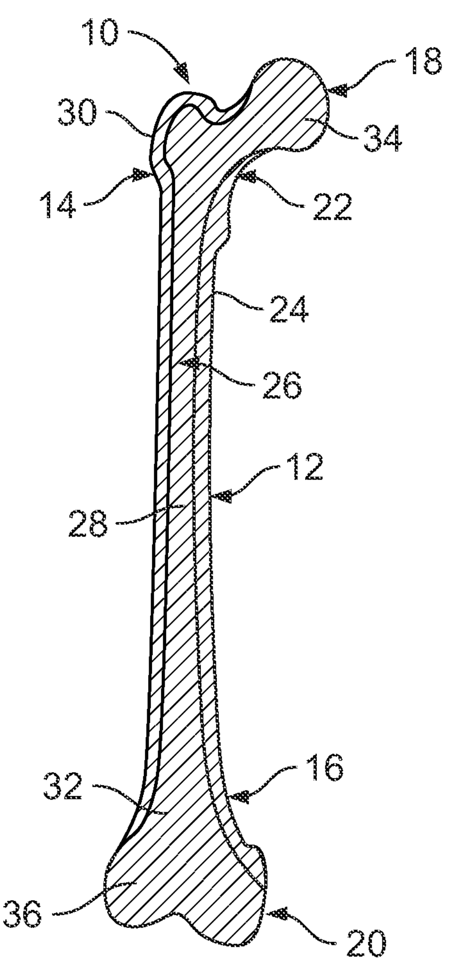
FIG. 1 is cross section view of a femur.

FIG. 1 illustrates a femur 10 and its six anatomical regions: a diaphysis or midshaft 12, proximal metaphysis 14, distal metaphysis 16, proximal epiphysis or head 18, distal epiphysis 20, and a femoral neck 22. The femur 10 includes a hard cortex 24 and a medullary cavity 26. The medullary cavity 26 includes a medullary canal 28 which runs through the center of shaft 12, as well as proximal and distal metaphyseal areas 30 and 32, and proximal and distal epiphyseal areas 34 and 36.

Figure 2:
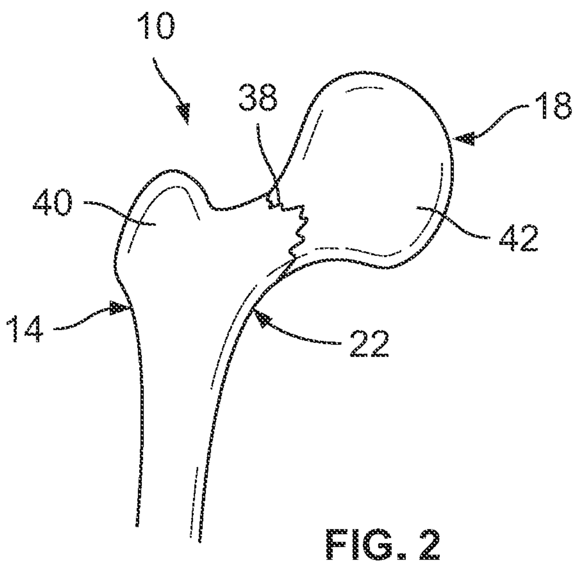
FIG. 2 is an anterior-posterior elevation view of a proximal femur having a femoral neck fracture.

FIG. 2 is an anterior-posterior view of a proximal portion of femur 10 having a fracture 38 extending along femoral neck 22. Fracture 38 separates the proximal femur into a first bone portion 40 adjacent the proximal metaphysis 14 and a second bone portion 42 adjacent the proximal epiphysis or head 18. Fracture 38 is an exemplary illustration of an unstable, extra-articular fracture, i.e., the fracture is located outside of a joint. This type of fracture, if not treated, can lead to long-term complications including comminution (i.e., pulverization of the bone), which may result in the shortening of femoral neck 22 and severe pain.

Figure 3:
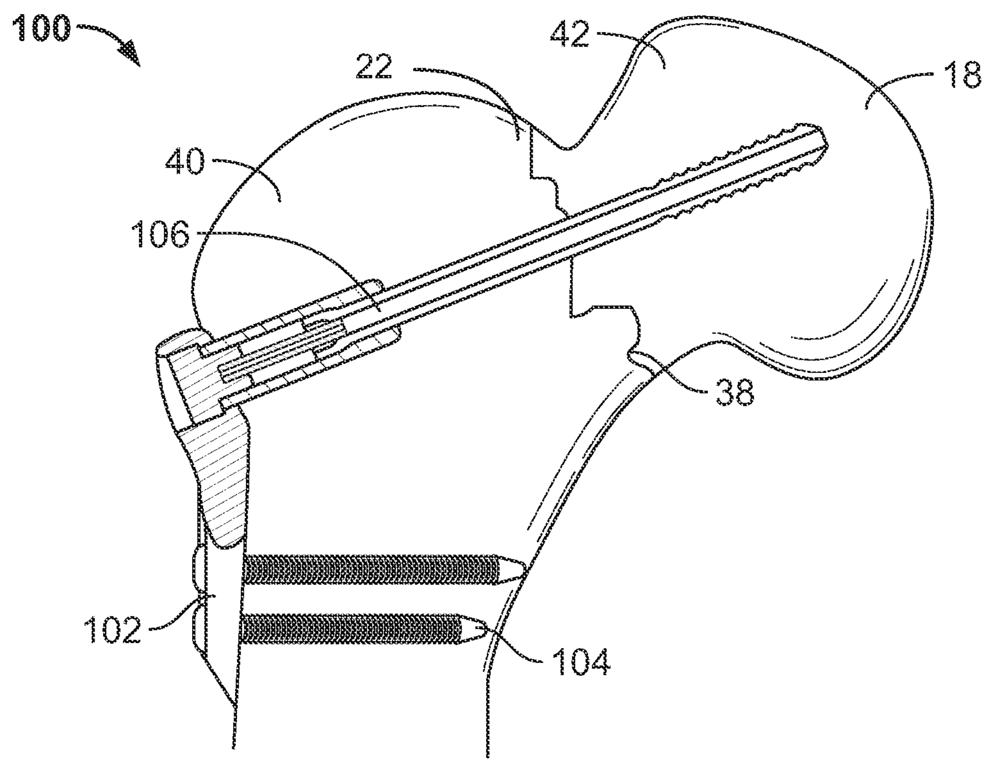
FIG. 3 is an anterior-posterior elevation view of a prior art fracture fixation device mounted on a proximal femur having a fractured neck.

Referring to FIG. 3, a prior art fracture fixation device 100 is shown for compressing first and second bone portions and for maintaining axial and rotationally stability between the first and second bone portions during healing of fracture 38. Fixation device 100 generally includes a bone plate 102, at least one cortical screw 104 for attaching an inferior portion of bone plate 102 to the subtrochantric shaft of femur 10 and at least one compression screw 106 for attaching a superior portion of bone plate 102 to the head 18 and neck 22 of femur 10 and for compressing fractured bone portions 40, 42 together. It will be appreciated that FIG. 3 shows a single compression screw 106 for clarity of the illustration, however, in practice a single compression screw or a plurality of compression screws may be utilized.

Figure 4:
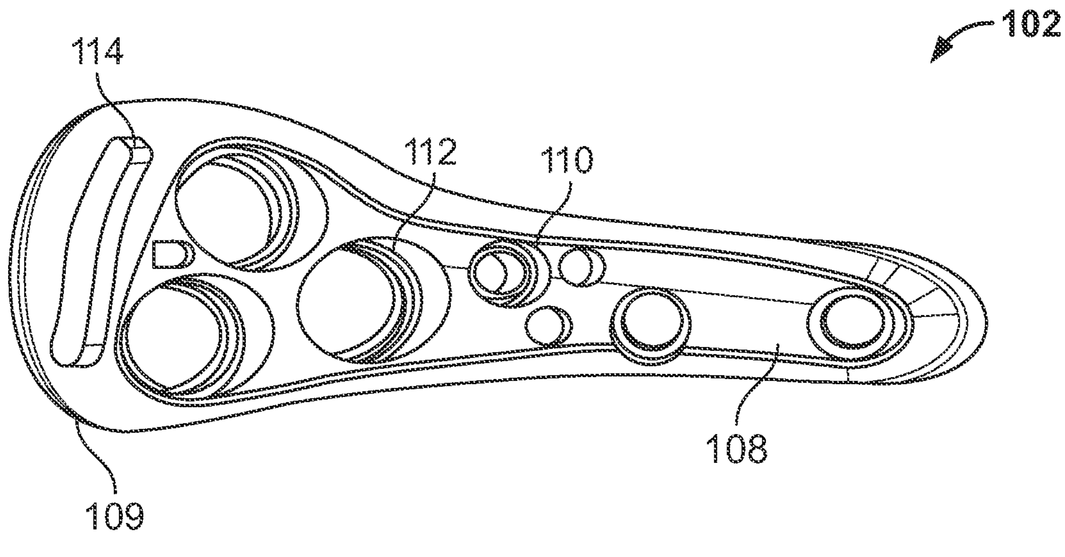
FIG. 4 is a front elevation view of a bone plate of the prior art fracture fixation device of FIG. 3.

Bone plate 102, as shown in FIG. 4, includes a first surface 108, a second surface 109 opposite the first surface, a plurality of threaded holes 110 defined in an inferior portion of the bone plate that are sized and configured to receive cortical screws 104, a plurality of threaded holes 112 defined in a superior portion of the bone plate that are sized and configured to receive compression screws 106 and a slot 114 configured to receive a guidewire. Second surface 109 may sometimes be referred to herein as a bone facing surface as it is shaped to lie against a proximal portion of femur 10, and more particularly on the proximal metaphysis 14 and the subtrochantric shaft of the femur.

Cortical screws 104 may have threads (not shown) on the periphery of a head of the cortical screw for engaging threads in cortical screw hole 110, thus preventing the cortical screw from backing out of bone plate 102. Slot 114 is shown formed in a superior most section of bone plate 102 and configured to receive a guide wire for facilitating proper positioning of the bone plate during a fixation procedure.

Each one of the compression screw assemblies described hereinafter are adapted to axially and rotational stabilize first bone portion 40 relative to second bone portion 42 during healing of fracture 38, thus preventing the shortening of femoral neck 22 and improving postoperative function of the hip. Furthermore, any one of the compression screw assemblies disclosed hereafter may be used with a plate similar to bone plate 102 and one or more cortical screws 104 as described above. The bone plate and cortical screws are thus not described in each embodiment. Instead, these features are merely renumbered with sequential 100 series numerals. For example, in describing various embodiments of the fracture fixation devices, the bone plate as described above will be referenced as bone plate 202, 302, 402, etc. Similarly, the cortical screws as described above will be referenced as cortical screw 204, 304, 404, etc. It is to be understood that although bone plate 102 is illustrated as having five cortical screw holes 110, in accordance with certain embodiments of the present invention, plates may have less than five cortical screw holes or more than five cortical screw holes. Similarly, although bone plate 102 is illustrated as having three compression screw holes 112, it will be appreciated that bone plates for use with the present invention may have less than three compression screw holes or more than three compression screw holes. Plates for use with the present invention may also include slots, like slot 114 located in other portions of the plate.

FIGS. 5A and 5B illustrate a fracture fixation device 200 adapted to improve stability and prevent relative axial and rotational movement between first bone portion 40 and second bone portion 42. Fixation device 200 includes a bone plate 202, at least one cortical screw (not shown), a compression screw housing 206 and a compression screw 208. Compression screw housing 206 may be a lag screw as shown in FIGS. 5A and 5B. However, compression screw housing 206 may alternatively be a barrel. That is, a surgeon may interchange compression screw housing 206 between a lag screw and a barrel, depending on the anatomical size and the stability requirement for fixation. As used herein, the term lag screw means a tubular housing having external threads on a shaft of the housing, whereas the term barrel means the tubular housing has a threadless shaft. In situations in which more than one compression screw is employed, a surgeon may choose between lag screws, barrels or a combination of lag screws and barrels.

Irrespective of whether compression screw housing 206 is a lag screw or a barrel, the housing may include an external thread disposed on a head or proximal end 210 of the housing to cooperate with the threaded compression screw opening of bone plate 202 for locking the compression screw housing to the bone plate. Compression screw housing 206 includes a cannulated sidewall that extends from proximal end 210 to distal end 212 and defines a bore 214. Housing 206 is shown having a stopper or an inwardly extending ledge 215 for preventing compression screw 208 from backing out of the compression screw opening of bone plate 202 as is explained in further detail hereinafter. Of course, housing 206 is not required to have a stopper or ledge 215.

Compression screw 208 is insertable into the bore 214 of compression screw housing 206 and selectively moveable through the bore. A collapsible and expandable anchoring member 216 is attached adjacent the distal end of compression screw 208 such that the anchoring member is axially advanceable from a first position in which the anchoring member is radially surrounded by housing 206 (FIG. 5A) to a second position in which the anchoring member extends from the housing 206 (FIG. 5B). Anchoring member 216 may include a plurality of triangular shaped prongs 219 that are biased radially outward and capable of being collapsed to be inserted through the threaded compression screw hole of bone plate 202 and into the bore 214 of housing 206, and then expanded to a natural or expanded condition upon axial advancement of the anchoring member from the bore of the compression screw housing (FIG. 5B) to engage bone.

In an alternative aspect, screw 208 can have a set of threads running along the length thereof for engagement with anchoring member 216. The threads along screw 208 can be rotationally opposite of the threads of housing 206 to prevent either screw from easily backing out. For example, the threads along screw 208 can have right-hand threads while the threads along housing 206 can have left-hand threads, or vice versa. In a further alternative aspect, anchoring member 216 may have any number of prongs 219 radially located about compression screw 208, such as only one set of prongs.

A stopping mechanism 218 is coupled to a proximal end 220 of compression screw 208 for preventing the compression screw from backing out of compression screw housing 206. In one embodiment, stopping mechanism 218 may include a plurality of leg members 222 pivotally attached to the proximal end 220 of compression screw 208 at a pivot point 224. Each one of the plurality of leg members 222 is capable of transitioning from a first position in which the leg members extend in a direction that is generally parallel to a longitudinal axis of compression screw 208 (FIG. 5A) to a second position in which each of the plurality of pivotal leg members extend radially away from the longitudinal axis of the compression screw (FIG. 5B). In one embodiment, the plurality of leg members 222 may define an interior surface having an internal thread 226.

Fixation device 200 is further shown including a conical wedge 228 for selectively controlling axial advancement of compression screw 208 and actuating stopping mechanism 218. More specifically, conical wedge 228 includes an external thread 230 for cooperating with the internal threading 226 of stopping mechanism 218 such that rotation of the conical wedge in a first direction (i.e., clockwise) advances the conical wedge toward compression screw 208 causing the plurality of legs 222 to expand radially outwardly. Further rotation of the conical wedge 228 against compression screw 208 will axially advance the compression screw toward the head 18 of femur 10.

FIGS. 6A and 6B illustrate a variant fracture fixation device 200' that includes each of the features of fracture fixation device 200 except as discussed below. As shown, in variant fixation device 200', compression screw housing 206' is a barrel. However, it will be appreciated that the compression screw housing may be either a barrel or a lag screw.

Compression screw housing 206' defines a slot 232' extending through a sidewall of the housing. Slot 232' is axially located between the proximal end 210' of housing 206' and the distal end 212' of the housing. In one embodiment, slot 232' is located approximately halfway between the proximal end 210' and the distal end 212' of housing 206'. In another embodiment, as shown in FIGS. 6A and 6B, slot 232' is located closer toward the proximal end 210' of housing 206', for example, approximately ⅓ of the length of the housing measured from the proximal end of the housing. Variant fracture fixation device 200' further includes a second anchoring member 234' in addition to anchoring member 216'. Anchoring members 216' and 234' are formed to include all of the same features of anchoring member 216 as described above with respect to FIGS. 5A and 5B. The second anchoring member 234' is disposed proximal anchoring member 216' and sized and configured to extend through slot 232' when the second anchoring member is axially advanced and positioned radially adjacent the slot.

Figures 7A, 7B:
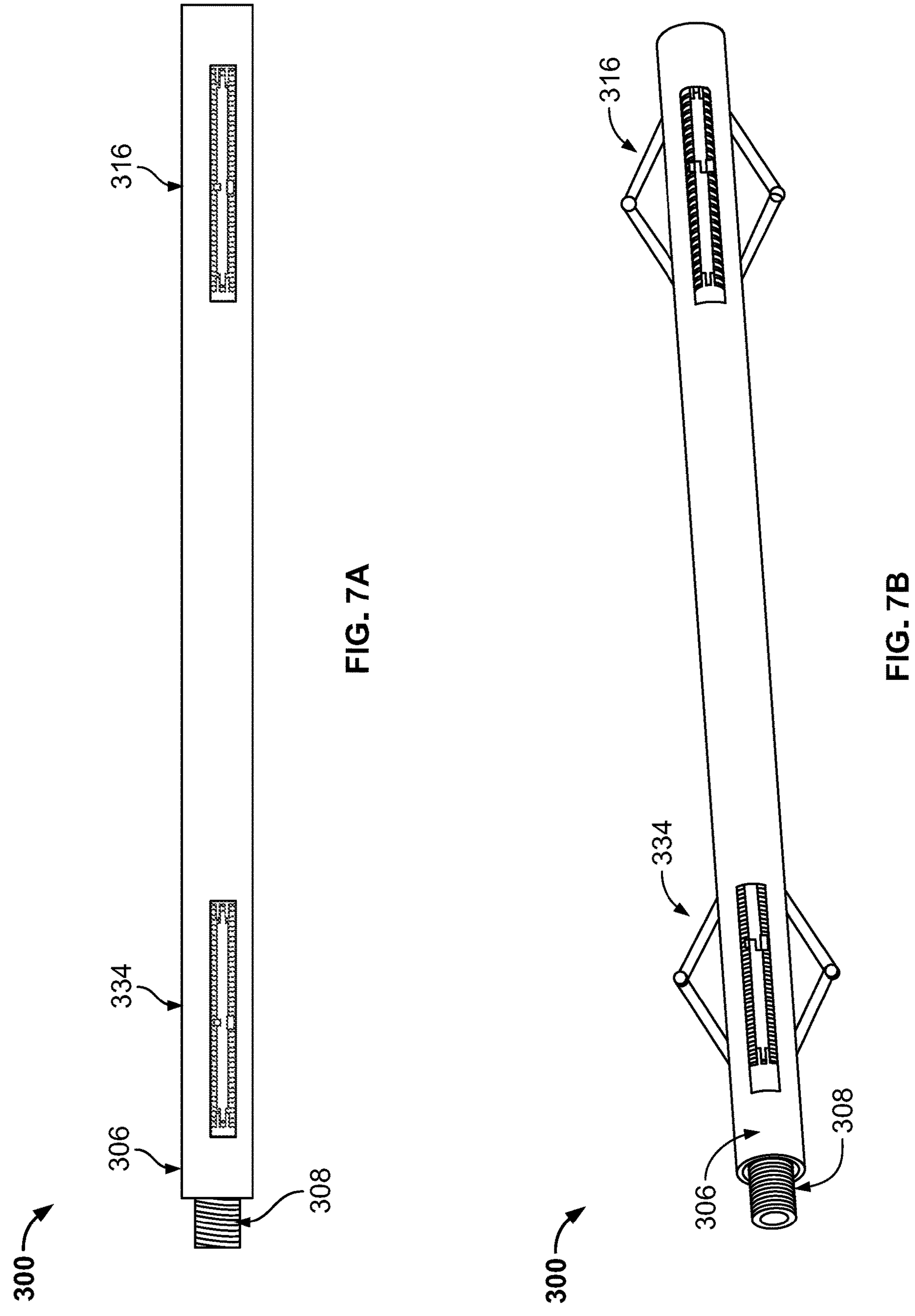
FIG. 7A is a side view of a fracture fixation device in a collapsed condition according to another aspect of the present disclosure.
FIG. 7B is a perspective view of the fracture fixation device of FIG. 7A in an expanded condition.

Turning to FIGS. 7A-7D, a fracture fixation device 300 is depicted that includes each of the features of fracture fixation device 200, 200' except as discussed below. FIG. 7A depicts fixation device 300 in a first unexpanded configuration with collapsible and expandable anchoring members 316, 334 within housing 306. FIG. 7B depicts fixation device 300 in a second expanded configuration after compression screw 308 has been rotated to expand anchoring members 316, 334 to extend exterior to housing 306.

Figure 7C:
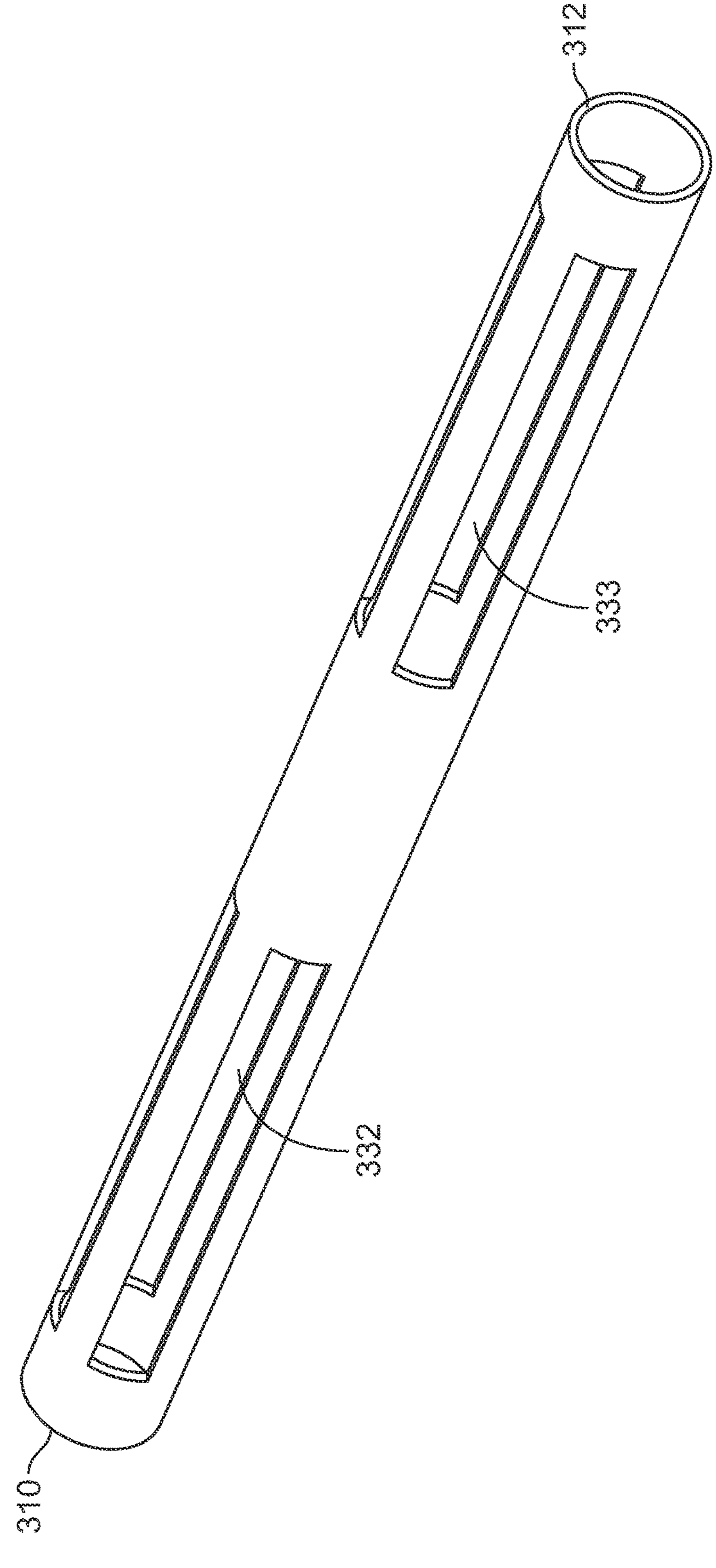
FIG. 7C is a perspective view of a housing of the fracture fixation device of FIG. 7A.

FIG. 7C depicts compression screw housing 306 on its own. As shown, housing 306 includes slots 332 configured to receive anchoring member 334 and slots 333 configured to receive anchoring member 316. Slots 332 are circumferentially arranged around housing 306 adjacent proximal end 310 while slots 333 are circumferentially arranged around housing 306 adjacent distal end 312. Compression screw housing 306 is depicted as being a barrel, however it will be appreciated that the compression screw housing may also be a lag screw, like in the embodiments discussed above. FIG. 7C depicts three slots 332, 333 equally spaced about housing 306, however, in alternative aspects, there may be more or less than three slots 332, 333 and/or slots 332, 333 may be unequally spaced about housing 306.

Figure 7D:
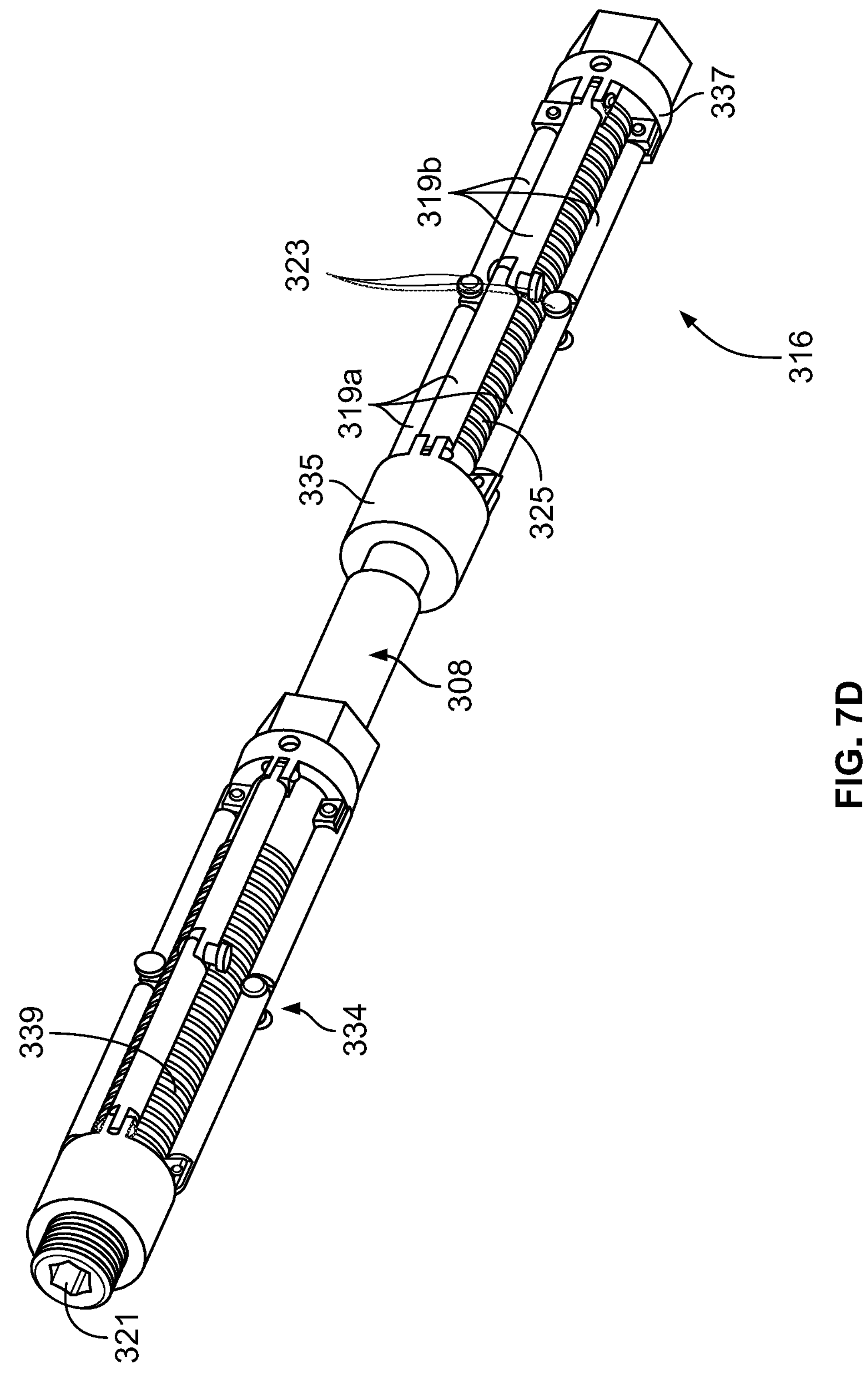
FIG. 7D is a perspective view of anchoring members of the fracture fixation device of FIG. 7A.

FIG. 7D depicts compression screw 308 and anchoring members 316, 334, without housing 306. Compression screw 308 includes a first set of threads 339 adjacent proximal end 310 of housing 306 and a second set of threads 325 adjacent distal end 312 of housing 306. In alternative aspects, there may be more or less than two sets of threads 325, 339. Compression screw 308 defines an opening 321 configured to receive an actuation tool, such as a hex key, Allen wrench, or the like. In this manner, rotation of the actuation tool can then rotate compression screw 308. Rotation of compression screw 308 axially drives the compression screw which, in turn, expands anchoring members 316, 334, as further described below.

Anchoring member 334 and anchoring member 316 share the same features except anchoring member 334 is adjacent proximal end 310 of housing 306 and threads 339 of compression screw 308, and anchoring member 316 is adjacent distal end 312 of housing 306 and threads 325 of compression screw 308. Anchoring member 316 includes a movable connector 335 rotatably connected to a proximal end of prongs **319*a* and a fixed connector 337 rotatably connected to a distal end of prongs 319*b*. A distal end of prongs 319*a* may be connected to a proximal end of prongs 319*b* through prong connectors 323. Fixed connector 337 is fixedly attached to housing 306 while movable connector 335 is slidable within housing 306. For example, fixed connector 337 may be secured to housing 306 through a press-fit engagement or other means capable of restricting the movement of the fixed connector. Moreover, connectors 335, 337 rotatably receive compression screw 308. In this manner, rotation of compression screw 308 can slide movable connector 335 within housing 306 while fixed connector 337** remain stationery.

FIG. 7D depicts the connections amongst prongs **319*a*, 319*b* and connectors 335, 337 as a hinge and pin connection, however, in alternative aspects, other connections may be used, such as a ball and socket connection, or any other connection allowing the prongs and connectors to move relative to each other. In this manner, as further described below, movement of movable connector 635 relative to fixed connector 337 in a distal direction can expand prongs 319*a*, 319*b* from an unexpanded configuration in which they are substantially parallel to an axis defined by compression screw 308 to an expanded configuration in which they are transverse to the axis. Conversely, movement of movable connector 335 in a distal direction would move prongs 319***a*, 319*b* from an expanded configuration to an unexpanded configuration.

Figure 8A:
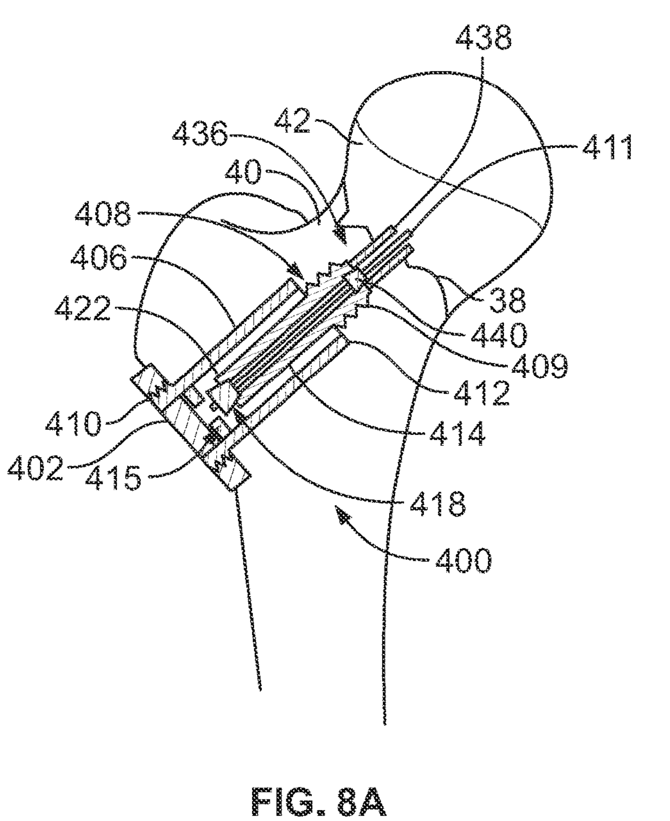
FIG. 8A is a schematic representation of a fracture fixation device mounted on a proximal femur having a radially expandable anchor in a collapsed condition according to another aspect of the present disclosure.
Figure 8B:
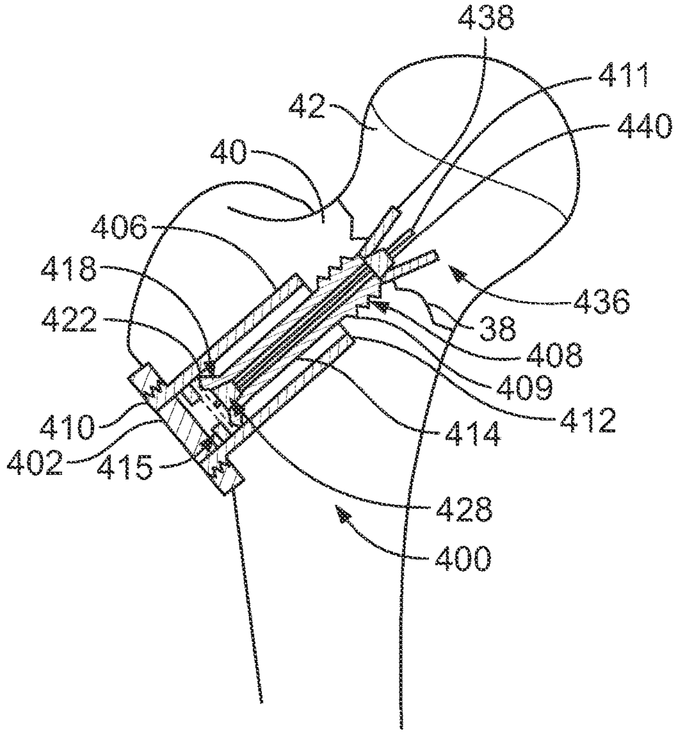
FIG. 8B is a schematic representation of the fracture fixation device of FIG. 8A showing the radially expandable anchor in the expanded condition.

FIGS. 8A and 8B illustrate another variant fracture fixation device 400 adapted to improve stability and prevent relative axial and rotational movement between first bone portion 40 and second bone portion 42. Fixation device 400 includes several of the features discussed above in connection with FIGS. 5A-5B, 6A-6B, and 7A-7D the further features described below. Fixation device 400 includes a bone plate 402, cortical screws (not shown), a compression screw housing 406 and a compression screw 408. In variant fixation device 400, compression screw housing is a barrel as illustrated in FIGS. 8A and 8B. However, it is understood that compression screw housing 406 may alternatively be switched out for a lag screw at the surgeon's preference.

Compression screw housing 406 includes an external thread disposed adjacent a head or proximal end 410 of the housing to cooperate with the compression screw hole (shown in FIG. 4) of bone plate 402 for locking the compression screw housing to the bone plate. Housing 406 includes a cannulated tubular sidewall that extends from proximal end 410 to distal end 412 and defines a bore 414. Housing 406 has a stopper or inwardly extending ledge 415 for preventing compression screw assembly 408 from backing out of the opening of bone plate 402.

Compression screw assembly 408 includes a cannulated lag screw 409 and a lead screw 411 disposed within the bore 414 of housing 406. More specifically, lead screw 411 is disposed within the cannula of lag screw 409 and moveable through the bore 414 of screw housing 406 independent from of lag screw 409. An anchoring member 436 is attached adjacent the distal end of lead screw 411. Anchoring member 436 includes a plurality of pivotal arms 438 attached to the distal end of the lag screw 409 and transitionable between a first condition in which the arm members extend substantially parallel to a longitudinal axis of the lag screw (FIG. 8A) and a second condition in which the arm members extend radially outward from the longitudinal axis of the lag screw (FIG. 8B).

A stopping mechanism 418, which is similar to stopping member 418, is coupled adjacent a proximal end of lag screw 409 for preventing the compression screw assembly 408 from backing out of the bore 414 of housing 406. Fixation device 400 further includes a conical wedge 428 for selectively controlling axial advancement of lead screw 411 and actuating stopping mechanism 418. Conical wedge 428 is constructed to cooperate with stopping mechanism 418 as explained with respect to conical wedge 428 and stopping mechanism 418 of FIGS. 5A and 5B. Variant fixation device 400 further includes a second conical wedge 440 attached adjacent the distal end of lead screw 411 for controlling the radial expansion of pivotal arms 438. That is, as lead screw 411 is advanced into anchoring member 436, conical wedge 440 engages pivotal arms 438 and forces the arms to radially expand and engage cancellous bone of femur 10.

Figure 9A:
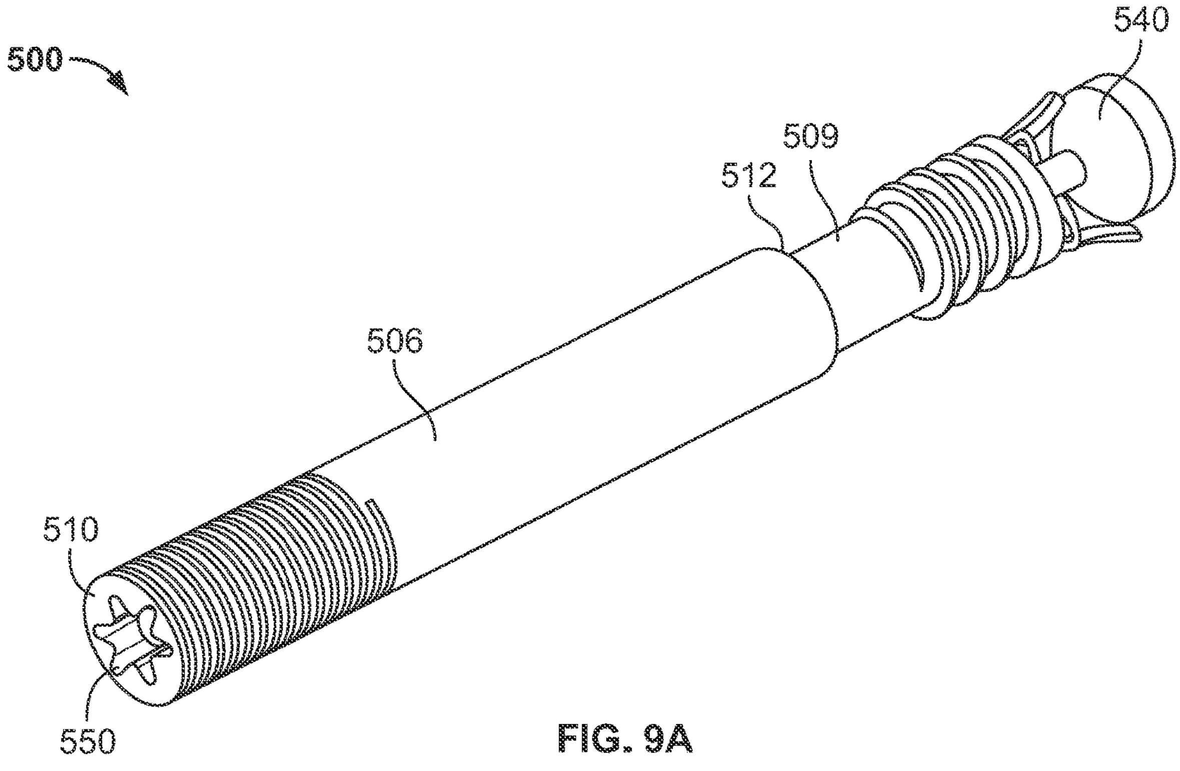
FIG. 9A is a perspective view of a fracture fixation device according to another aspect of the present disclosure.
Figure 9B:
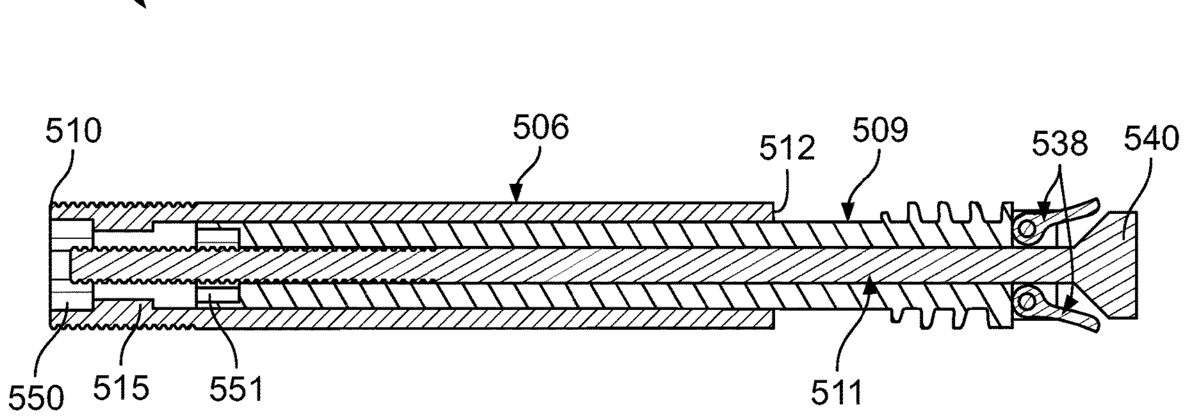
FIG. 9B is a cross-sectional view of the fracture fixation device of FIG. 9A.

In an alternative aspect, fixation device 400 may not have a proximal wedge 428 or expanding legs 422. For example, FIGS. 9A-9B depicts fracture fixation device 500 in an unexpanded configuration that includes each of the features of fracture fixation device 400 except as discussed below. FIG. 9A depicts an isometric view of fracture fixation device 500. FIG. 9B depicts a cross-sectional view of fracture fixation device 500.

Recess 550 is configured to receive a first instrument to engage and rotate housing 506 to be secured to a bone plate, such as bone plate 202, 202', 300, 400. Recess 551 is configured to receive a second instrument to engage and rotate lag screw 509 to be secured into a surrounding bone surface, such as bone portion 42. Lead screw 511 includes a set of proximal threads to be engaged and rotated to axially move the lead screw. In this manner, fixation device 500 transitions from an unexpanded configuration to expanded configuration as lead screw 511 proximally moves. Collapsible and expandable anchoring member 536 are arms that are hingedly connected to lag screw 509 such that wedge 540 of lead screw 511 can engage anchoring member 536 to expand and engage the surrounding bone area as the lead screw is proximally moved. Housing 706 defines an extending ledge 515 to set a maximum compression distance (e.g., 5-10 mm) for the proximal end of lag screw 509 to abut against as the proximal movement of lead screw 511 proximally moves lag screw 509. Preferably, housing 506 has a diameter of 11 mm, lag screw 509 has a diameter of 8.2 mm, and lead screw 511 has a diameter of 6 mm, however, in alternative aspects, each of the diameters may be larger or smaller.

Figure 10:
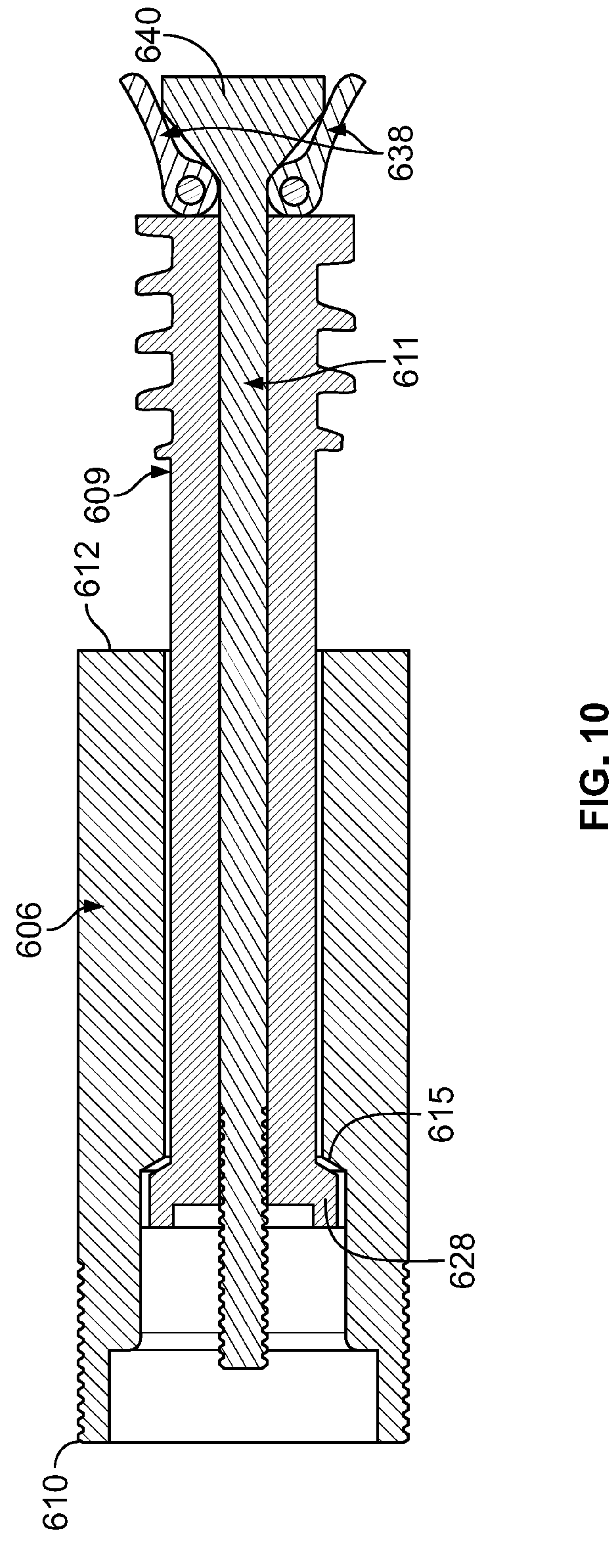
FIG. 10 is a cross-sectional view of a fracture fixation device according to another aspect of the present disclosure.

In a further alternative aspect, housing 506 can set a maximum distance for distal advancement of lead screw 511 in addition to, or instead of, a maximum compression distance for proximal movement of the lead screw. For example, FIG. 10 depicts a cross-sectional view of fracture fixation device 600 in an expanded configuration having a housing 606 defining a ledge 615 to contact wedge 628 of lag screw 609 and set a maximum distance for distal advancement of the lag screw. In a yet further alternative aspect, either of fixation devices 500, 600 may include a wedge and/or expanding legs, as shown in FIGS. 8A-8B.

The use of fixation devices 200, 200' and 400 to compress and stabilize the fractured bone portions 40, 42 together to heal fracture 38 will now be described with reference to FIGS. 5A-6B and 8A-8B. In use, a surgeon first attaches bone plate 202, 202', 402 to a proximal femur by fastening the cortical screws through the cortical screw holes 110 (FIG. 4) and into the femur. A surgeon then secures one or more bone compression housings 206, 206', 406 to bone plate 202, 202', 402' by inserting the housings through threaded holes 112 (FIG. 4) and connecting the threading on the proximal end of the housing to the internal threading of the openings. Next, the surgeon collapses the anchoring member 216, 216', 234', 438 (or selects an already collapsed component) and inserts compression screw 208, 208', or compression screw assembly 436 into the bore 214, 214', 414 of housing 206, 206', 406 and rotates the compression screw to axially advance the screw into the neck 22 of femur 10 until the underside of the bone compression screw sits in the screw hole.

With specific reference to FIGS. 5A-6B, compression screw 208, 208' is then further rotated to apply compression to the fracture site. Such rotation drives compression screw 208, 208' in an axial direction towards the head 18 of femur 10 and radially expands the plurality of leg members 222, 222'. As a result, compression screw 208', 208' will be prevented from backing out from the neck 22 of femur 10 as leg members 222, 222' contact stopper 215, 215' and prevent the compression screw or compression screw assembly from backing out of the bore of compression screw housing 206, 206'.

With continued focus on fixation devices 200, 200', axial advancement of compression screw 208, 208' causes anchoring member 216, 216' to engage bone. More specifically, as anchoring member 216, 216' is pushed from bore 214, 214', prongs 219, 219' automatically expand to their neutral condition and engage cancellous bone. As prongs 219, 219' engage bone, the prongs compress first bone portion 40 and second bone portion 42 together and axially and rotationally stabilize the bone portions relative to one another. With specific reference to fixation device 200' and FIGS. 6A and 6B, axial movement of compression screw 208' will also cause second anchoring member 234' to extend through slot 232'. That is, second anchoring member 234' remains compressed in its collapsed condition as the second anchoring member is distally advanced until the second anchoring member is positioned at a location radially adjacent the slot 232'. Once the second anchoring member 234' has been axially advance so as to be radially adjacent slot 232', the second anchoring member will expand radially through the slot and engage bone to provide additional axial and rotational support to fractured bone portions 40, 42.

With reference to FIGS. 7A-7D and fixation device 300, a surgeon inserts an actuation tool (not shown) within opening 321 of compression screw 308. The surgeon then rotates the actuation tool to axially move compression screw 308. As compression screw 308 is axially moved, the respective movable connectors of anchoring members 316, 334 correspondingly slide within housing 306 to move toward the respective fixed connectors such that prongs 319*a*, 319*b* expands through slots 332, 333 exterior to the housing and engages the surrounding bone surface.

With reference to fixation device 400 and FIGS. 8A-8B, axial advancement of lead screw 411 will cause anchoring member 436 to radially expand. More specifically, a surgeon may rotate conical wedge 428 to axially advance lead screw 411 relative to lag screw 409. As lead screw 411 is advanced, conical wedge 440 engages pivotal arms 438 of anchoring member 436 and forces the arms to radially expand into the cancellous bone of femur 10. This engagement compresses first bone portion 40 and second bone portion 42 and rotationally stabilizes the bone portions relative to one another during healing of fracture 38.

With reference to fixation device 500 and FIGS. 9A-9B, a first actuation tool is inserted within recess 550 to engage housing 506 and secure the housing to a bone plate, such as bone plate 202, 202', 402. Once housing 506 is secured to the bone plate, a second actuation tool is inserted within recess 550 to engage and advance lag screw 509 into engagement with a bone portion, such as bone portion 42. Once lag screw 509 is engaged with the bone portion, the surgeon may engage a third actuation tool with lead screw 511 to rotate the lead screw and expand anchoring member 536 to engage the surrounding bone surface. Continued proximal movement of lead screw 511 proximally moves lag screw 509 with respect to housing 506 and compresses the fractured bone portions together until a desired compression has been reached or a proximal end of lag screw 509 abuts against ledge 515.

Alternatively, with reference to FIG. 10, the method of using fixation device 600 is similar to fixation device 500 except lag screw 609 can be distally advanced until wedge 628 abuts against ledge 615 prior to proximal rotation of lead screw 611.

FIGS. 11A and 11B illustrate a fracture fixation device 700 in accordance with yet another embodiment of the invention. Fixation device 700 includes a bone plate 702, at least one cortical screw (not shown), a compression screw housing 706 and a compression screw or pin 708.

Compression screw housing 706 may be a barrel or a lag screw having a cannulated sidewall that is inwardly angled toward its longitudinal axis from a proximal end 710 of the housing 706 to a distal end 712 of the housing. Compression screw housing 706 may have an external thread disposed on the head or proximal end 710 of the housing that is configured to cooperate with the threaded compression screw hole of bone plate 702, similar to holes 112 as shown in FIG. 4. The cannulated sidewall of housing 706 defines a bore 714. Housing 706 also includes a stopper or a pair of lugs 715 that extend inwardly into the bore 714 at a location adjacent the proximal end 710 of the housing for preventing compression screw 708 from retreating out of the bore 714 of housing 706.

Compression screw 708 is insertable into the bore 714 of housing 706. A collapsible and expandable anchoring member 716 is attached to the distal end of compression screw 708 such that the anchoring member is extendable through the distal end 712 of housing. Anchoring member 716 includes a plurality of fingers 718 spaced about a circumferential edge of compression screw 708. For example, anchoring member 716 is shown having three fingers 718 spaced 120 degrees from one another about the circumferential edge of compression screw 708. Alternatively, anchoring member 716 may include four fingers 718 spaced 90 degrees from one another about the circumferential edge of compression screw 708. In other configurations, anchoring member 716 may include less than three fingers 718 or more than four fingers, which may be equally or non-equally spaced about the circumferential edge of compression screw 708. As illustrated in FIGS. 11A and 11B, the plurality of fingers 718 are spaced apart from one another such that a gap is formed between adjacent fingers. The gap allows fingers 718 to flex inwardly (i.e., toward the longitudinal axis of compression screw or pin 708) and assists the user in advancing anchoring member 716 through the distal end 712 of housing 706.

Although the different embodiment components disclosed herein are preferably formed from biocompatible materials, compression screw 708 may be formed from biocompatible materials that are capable of self-expansion, for example, shape memory alloys such as nitinol or other Nickle-Titanium (Ni—Ti). As a result, compression screw 308 will expand as the compression screw is heated by the patient's body temperature such that compression screw will be prevented from moving proximally by stoppers or lugs 715 and backing out of the compression screw holes of bone plate 702.

Moreover, fingers 718 are capable of transitioning from a collapsed condition in which the plurality of fingers extend radially inward to an expanded condition in which the fingers expand in the radial direction. For example, FIG. 11C depicts fixation device 700' with only an intermediate portion of fingers 718' in an expanded configuration having a substantially curved shape. FIG. 11D depicts fixation device 700" with a distal portion of fingers 718" in an expanded configuration having a substantially curved shape. In alternative aspects, the expanded configuration of fingers 718, 718', 718" can have a shape with an acute angle rather than being substantially curved. Alternatively, fingers 718, 718', 718" can have an undulating shape with a number of curves or angles along the length thereof.

A ring or circlip 720 may optionally be placed about the plurality of fingers for controlling the expansion of the fingers, as shown in FIGS. 11A-11B. Ring 720 may be attached or formed along a length of one of fingers 718 such that ring 720 may limit the expansion of the fingers without sliding or moving along an axial direction.

The use of fixation device 700, 700', 700" to axially and rotationally stabilize the first bone portion 40 relative to the second bone portion 42 will now be described with reference to FIGS. 11A-11D. A surgeon first attaches bone plate 702 to proximal femur 10 using cortical screws and then secures housing 706 to the bone plate. Next, the surgeon inserts compression screw 708 into the bore 714 of housing 706 and rotates the compression screw to axially advance the screw into the neck 22 of femur 10 beyond the distal end 712 of the housing. Once positioned inside the patient's femur, the compression screw 708 automatically expands as the nitinol is radially warmed to body temperature. Expansion of the compression screw ensures that the screw will not back out from the neck 22 of femur 10 even under a force as the expanded proximal end of the screw is prevented from moving beyond lugs 715. Arm members 718, 718', 718" will also automatically expand in the radial direction and engage cancellous tissue as the temperature of compression screw 708 rises. As arm members 718, 718', 718" expand radially and engage bone, the arm members provide axial and rotational stability to fractured bone portions 40, 42.

FIGS. 12A-12G illustrate a fixation device 800 for the stabilization of a proximal femoral fracture in accordance with another embodiment of the invention. Fixation device 800 includes a bone plate 802, at least one cortical screw (not shown), a compression screw housing 806 and a compression screw 808.

Compression screw housing 806 may be a cannulated barrel or a cannulated lag screw configured to receive compression screw 808. An external thread is disposed on a head or proximal end 810 of the housing for securing the housing to the threaded compression screw hole of bone plate 802, similar to holes 112 as shown in FIG. 4.

Figures 12D, 12E:
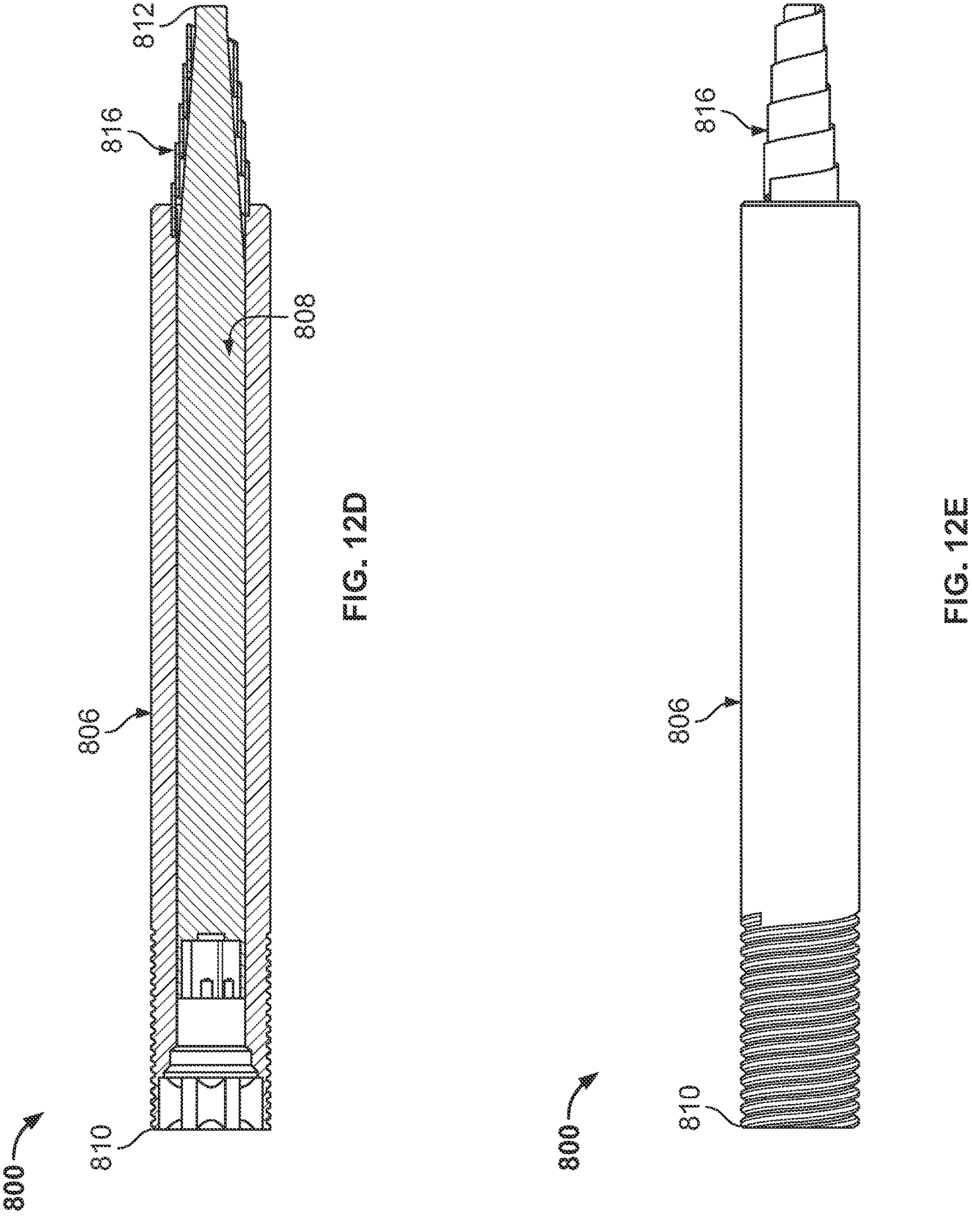
FIG. 12D is a cross-sectional view of the fracture fixation device of FIG. 12A in a collapsed condition.
FIG. 12E is a side view of the fracture fixation device of FIG. 12A in a collapsed condition.

The proximal end of compression screw 808 includes a head configured to receive an instrument, for example, a screw driver for rotating the compression screw and driving the screw toward the head 18 of femur 10. A collapsible and expandable anchoring tip 816 is attached to the distal end 812 of the compression screw 808. As shown in FIG. 12D, distal end 812 is a frustoconical shape, however, in alternative aspects, other shapes may be used, such as a spherical, cuboid, or the like. Collapsible and expandable anchoring tip 816 is an elongated and resilient material that is twisted or wound upon itself such that the anchoring tip forms a serrated and substantially frustoconical shape to conform to distal end 812 in its wound configuration. In one embodiment, the screw and anchoring tip are connected via a laser beam welding process, or the like. The elongated material may be a medical grade metal having a thickness of approximately 0.5 mm. In alternative aspects, tip 816 may be made of other materials, such as medical grade plastics or the like, and have a thickness greater or less than 0.5 mm.

Figures 12F, 12G:
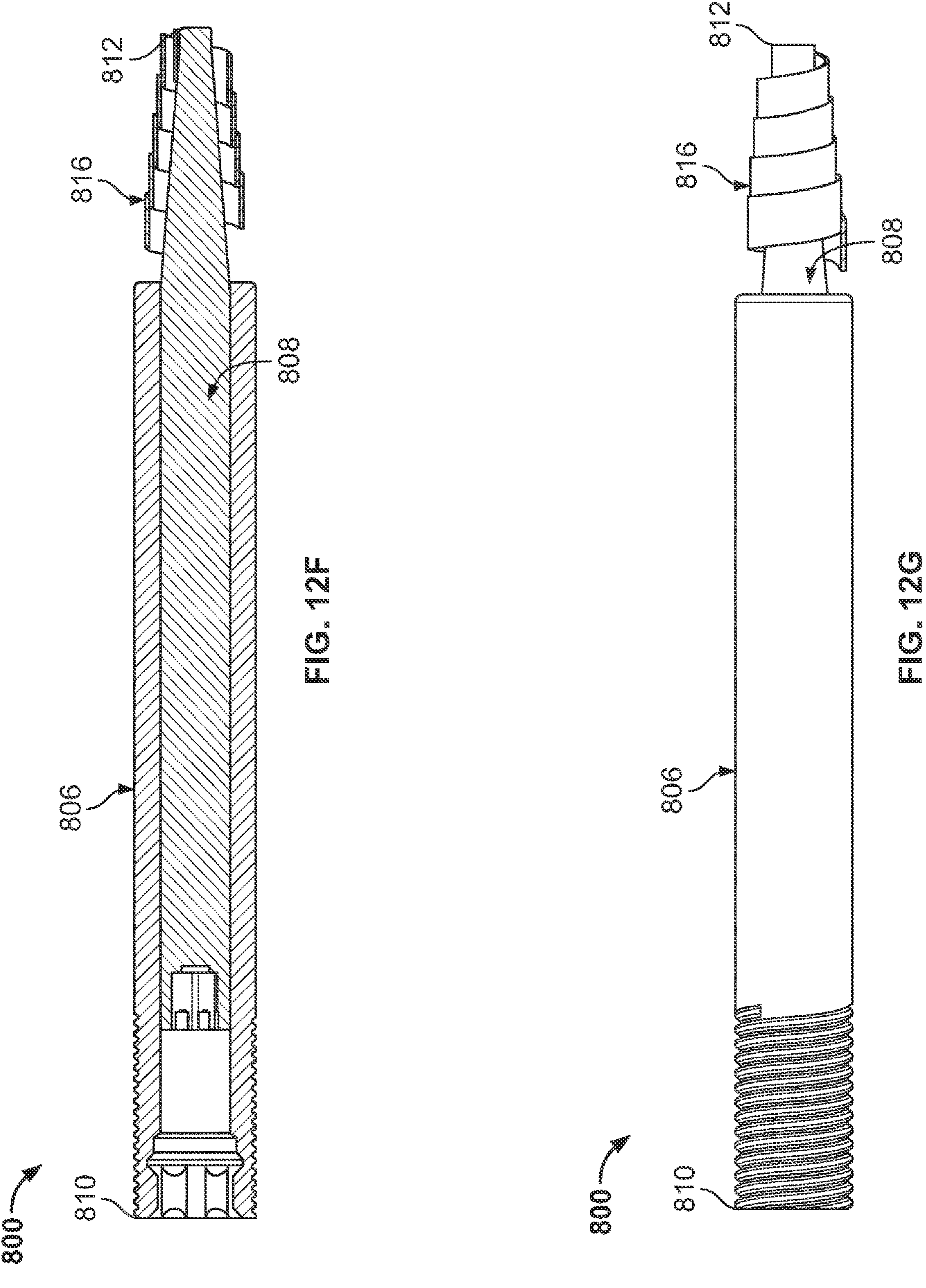
FIG. 12F is a cross-sectional view of the fracture fixation device of FIG. 12A in an expanded condition.
FIG. 12G is a side view of the fracture fixation device of FIG. 12A in an expanded condition.

Collapsible and expandable anchoring tip 816 is therefore capable of collapsing when compression screw is rotated in a first direction as the resilient material is wound upon itself, as shown in FIGS. 12A and 12D-12E, and then expanding to a normal state when the rotational force is released. In the expanded condition, as shown in FIGS. 12B and 12F-G, a base of anchoring tip 816 expands to a diameter that is larger than a diameter of the bore of housing 806 preventing the anchoring tip from retracting into the bore and backing out of the femoral neck.

In one embodiment, the initial diameter of anchoring tip 816 is oversized compared to that of the barrel diameter. Before insertion, the tip is collapsed (by manually applying a compressive force) to a size smaller than that of barrel size. This allows easy gliding of the screw and welded tip inside the barrel. After insertion, body temperature heats up the tip and reverses the compressive strain by radial expansion. When the tip radially expands to a diameter larger than that of the barrel diameter, the screw is prevented from proximally backing out.

For better locking of the tip against rotation, the proximal end of the bone can be prepared with an oversized bore to accommodate radial expansion of the tip. A suitable reamer instrumentation is needed to create a stepped bore for fixing of the barrel length (small diameter) and screw tip (large diameter).

Removal of the screw and tip needs to be done by rotating in the opposite direction. The removal by just rotation in the opposite direction would be difficult due to bone growth. This can be addressed by using a hollow screw, which helps to loosen up the bone growth by drilling through the hollow screw. Loosening up of the tip end from the bone can be achieved by a range of drilling holes.

The use of fixation devices 800 will now be described with reference to FIGS. 12A-12G. A surgeon first attaches bone plate 802 to proximal femur 10 using cortical screws. After bone plate 802 has been affixed, the surgeon inserts housing 406 through the compression screw holes (as shown in FIG. 4) and fastens the threading of the compression screw housing to the threaded opening to secure the housing to the bone plate. Next, the surgeon inserts compression screw 808 into the bore of housing 806 and rotates the compression screw to axially advance the screw beyond the distal end 812 of housing 806 and into the neck 22 of femur 10. The serrations of anchoring tip 816 assist the surgeon in cutting bone and axially advancing compression screw 808 toward the head 18 of femur 10. The surgeon then continues to rotate compression screw 808, for example, clockwise until anchoring tip 816 is desirably positioned.

Once in position, the surgeon may release the rotational tension which will allow anchoring tip 816 to radially expand. Radial expansion of the base portion of anchoring tip 816 ensures that the screw will not back out from the neck 22 of femur 10 even if a proximal force is applied. Moreover, as anchoring tip 816 radial expands and engages cancellous tissue, the tip provides axial and rotational stability to the fractured bone portions 40, 42.

FIGS. 13A-13D illustrate a fracture fixation device 900 in accordance with yet another embodiment of the invention. Fixation device 900 generally includes a bone plate 902, at least one cortical screw 904, a pin housing 906 and a compression screw or pin 908.

Figure 13A:
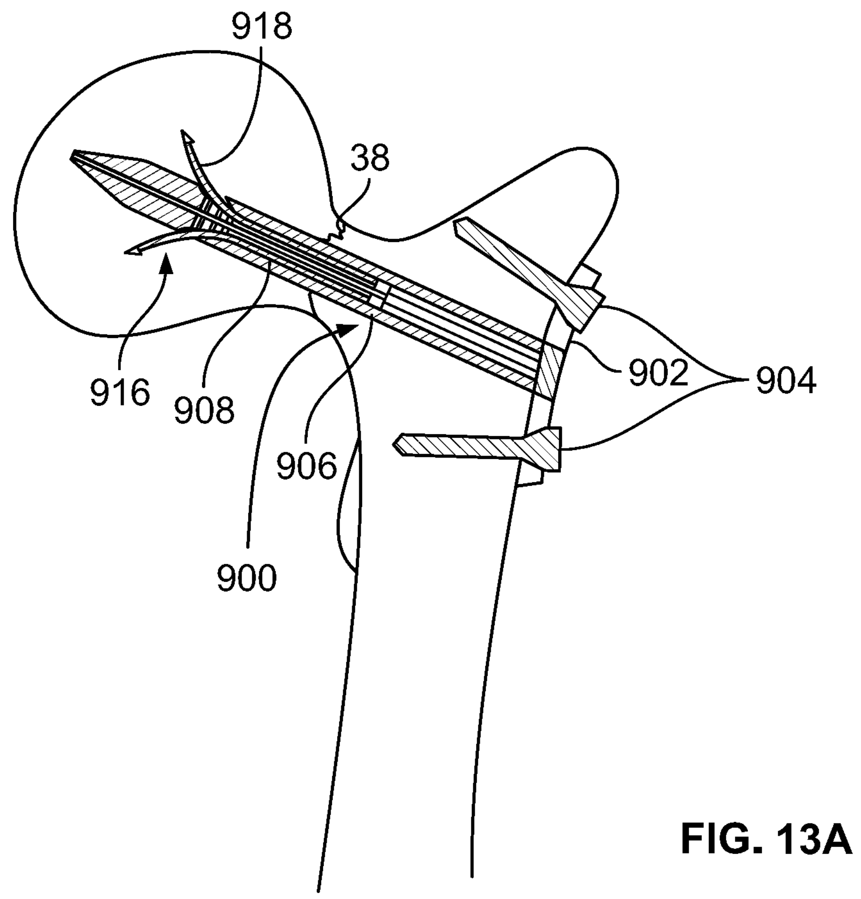
FIG. 13A is a schematic representation of a fracture fixation device secured to a proximal femur having a flexible anchoring member according to another aspect of the present disclosure.
Figure 13B:
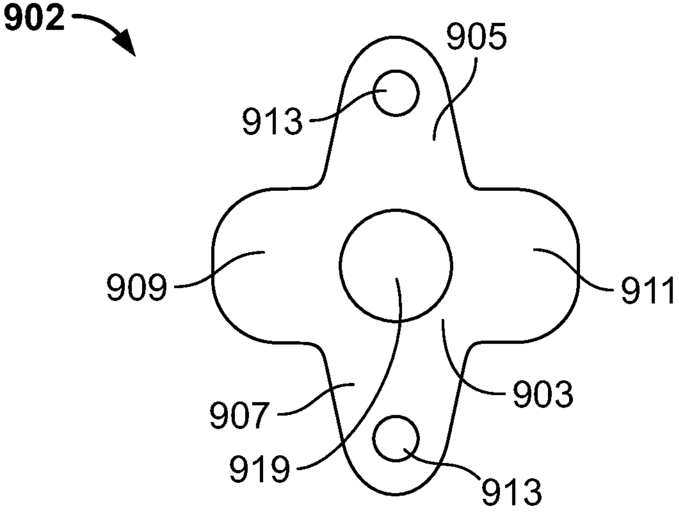
FIG. 13B is a schematic front elevation view showing the bone plate of FIG. 10A.

Bone plate 902, as shown in FIG. 13A, includes a bone facing surface that is laterally curved in an inferior to superior direction such that the bone facing surface is anatomically shaped to lie against the proximal femur of a majority of the general population. With reference to FIG. 13B, bone plate 902 as shown is substantially cross-shaped such that the bone plate includes a central region 903 and four wings: a superior wing 905, an inferior wing 907, an anterior wing 909 and a posterior wing 911. Bone plate 902 defines an opening 913 in superior wing 905 and inferior wing 907 configured to receive a cortical screw 904 for fastening the bone plate to the proximal femur and an opening 919 for coupling pin housing 906.

With reference to FIGS. 13A-13B, the curvature of bone plate 902 diverges each of the cortical screws 904 along different axis and improves rotational stability. That is, the inferior cortical screw extends substantially in the lateral to medial direction while the superior cortical screw extends in both the lateral to medial direction and the inferior to superior direction. Openings 913 may be threaded to engage a threaded head of the cortical screw as is known in the art. Anterior wing 909 and posterior wing 911 are shaped to engage anterior and posterior regions of the proximal femur to prevent rotational movement of the fixation device. Although FIG. 13B depicts only wings 905, 907 having openings 913, in alternative aspects, each wing 905, 907, 909, 911 can have more than three opening 913.

Figure 13C:
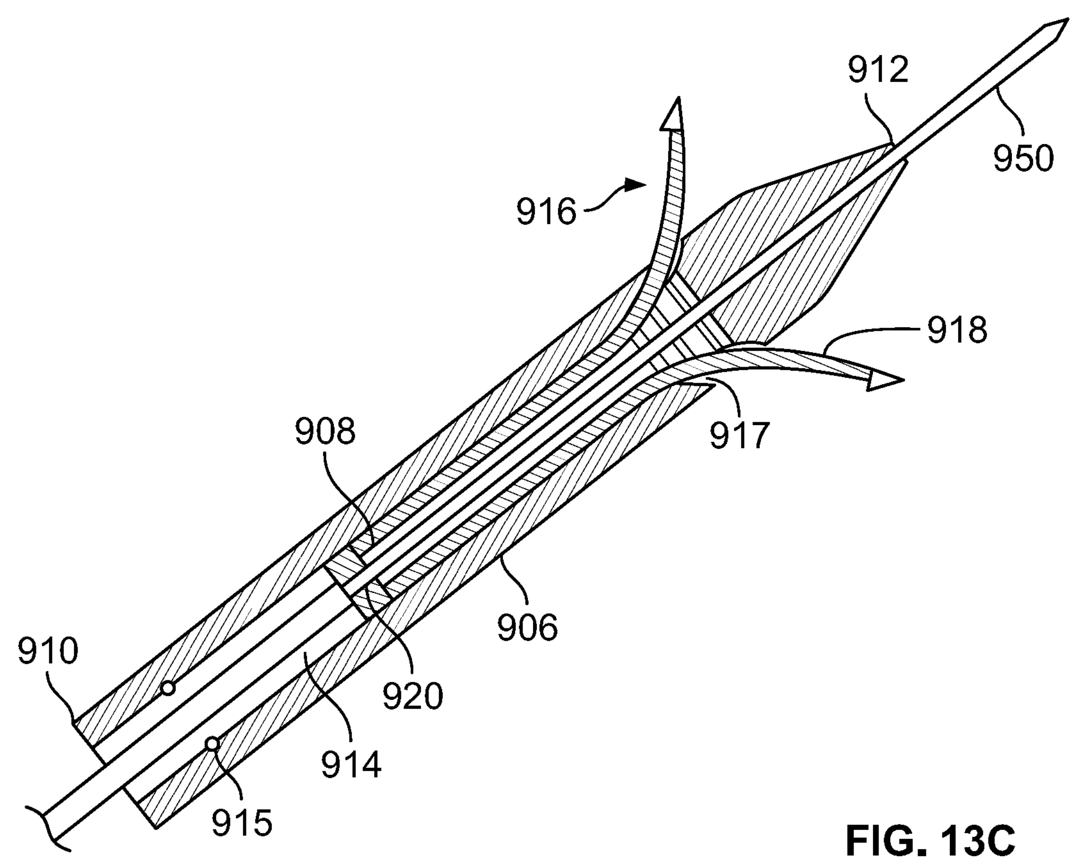
FIG. 13C is a schematic side elevation view of the pin housing and the pin of the fracture fixation device of FIG. 10A with a k-wire extending through the pin.

Pin housing 906, as shown in FIGS. 13A and 13C, is a cannulated barrel having a sidewall extending between a proximal end 910 and a distal end 912. The head or proximal end 910 of pin housing 906 is provided with a thread for cooperating with the threaded opening 919 of bone plate 902 to secure the pin housing to the base plate. Pin housing 906 also includes an inwardly extending ledge 915 adjacent the proximal end 910 of the pin housing for preventing pin 908 from backing out of the housing. As shown in FIG. 13C, the sidewall of pin housing 906 defines a plurality of outwardly arching tracks 917 extending between the bore 914 of the pin housing and through the external surface of the sidewall.

Figure 13D:
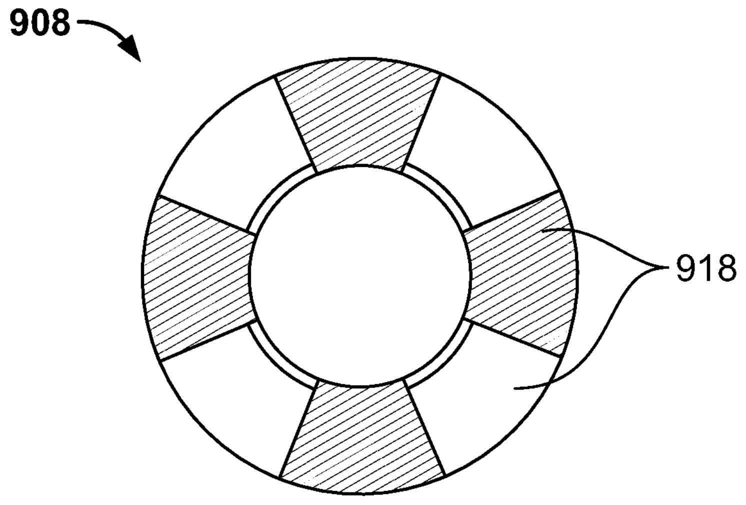
FIG. 13D is a schematic front elevation view of the pin of fracture fixation device of FIG. 10A.

Pin 908 is an elongated member having a collapsible and expandable anchoring member 916 provided at a distal end of the pin. Guidewire 950 runs through housing 906 and pin 908. Anchoring member 916 includes a plurality of fingers 918 disposed about a circumferential edge of pin 908. Anchoring member 916 may, for example, include four fingers 918 spaced 90 degrees from one another about the circumferential edge of pin 908 as shown in FIG. 13D. In other configurations, anchoring member 916 may include more or less than four fingers 918, which may be equally or non-equally spaced about the circumferential edge of compression screw 904. Each one of the fingers has an attached end connected to the distal end of pin 908 and a free end opposite the attached end that extends radially outwardly with respect to a longitudinal axis of the pin.

Each one of fingers 918 may be formed, for example, from a compliant metal and capable of transitioning from a collapsed condition in which the plurality of fingers 918 may be inserted through opening 919 and into the bore 914 of pin housing 906 and then radially expanded to extend through tracks 917.

The proximal end of pin 908 includes a tapered and compliant stopper 920 formed, for example, from a rubber material for engaging the inwardly extending ledge 915 and preventing the pin from backing out from the bore 914 of pin housing 906. Pin 908 may be cannulated for, and configured to receive, other instruments aside from guidewire 950, such as a k-wire, or other instrument, to allow a surgeon to properly align the pin during operation.

Figure 14A:
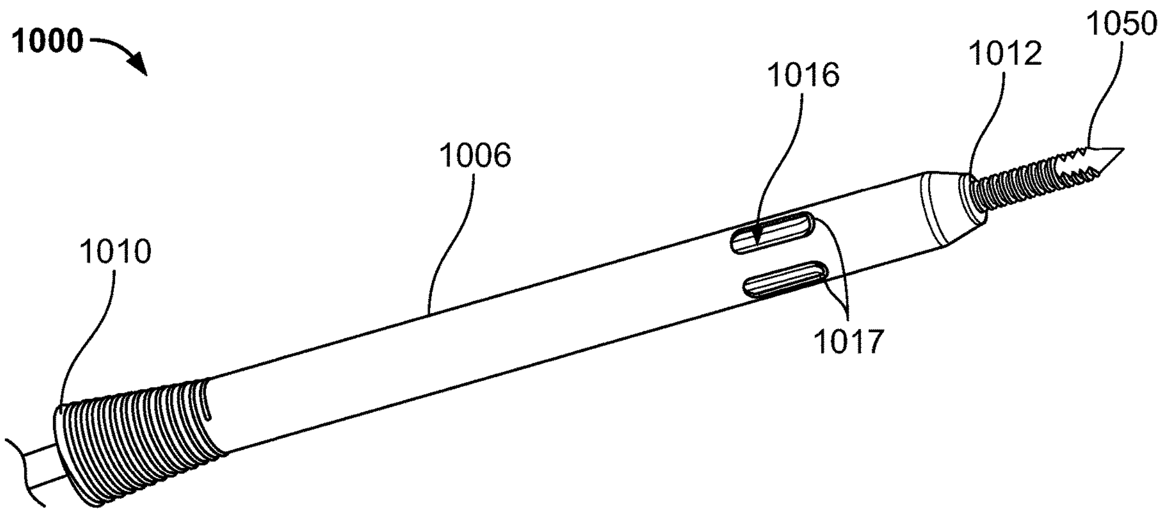
FIG. 14A is a perspective view of a fracture fixation device according to another aspect of the present disclosure.

In an alternative aspect, housing 906 and fingers 918 can have other shapes. For example, turning to FIGS. 14A-14B, housing 1006 has a smooth bore 1014 with no ledge, such as ledge 915 above, and a guidewire 1050 received within the bore. Moreover, housing 1006 is depicted as having proximal threads with a frustoconical shape distally tapering from proximal end 910. In this manner, housing 1006 can better engage with a bone plate, such as bone plate 902. Alternatively, where bone plate 902 is not used, the frustoconical shape allows for better engagement with the bone. In a further alternative aspect, threads of housing 1006 can have a cylindrical shape with a larger radius than the rest of housing 1006, a cone shape tapering from a distal point towards the proximal end, or the like.

Figure 14B:
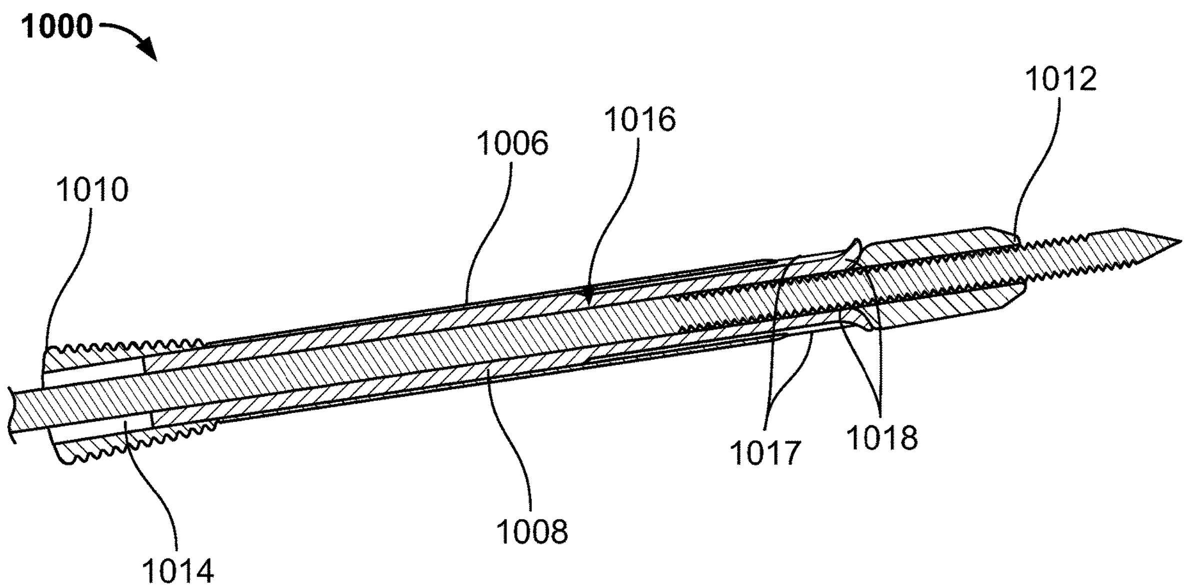
FIG. 14B is a cross-sectional view of a fracture fixation device of FIG. 14A.

FIG. 14B depicts fixation device 1000 in an un-expanded configuration, and collapsible and expandible anchoring member 1016 with curved fingers 1018. Fingers 1018 are configured to rest adjacent the distal surfaces of tracks 1017. In this manner, when pin 1008 of anchoring member 1016 is distally moved, the curvature of fingers 1018 may press upon and ride the distal surface of tracks 1017 to smoothly expand.

Figure 15A:
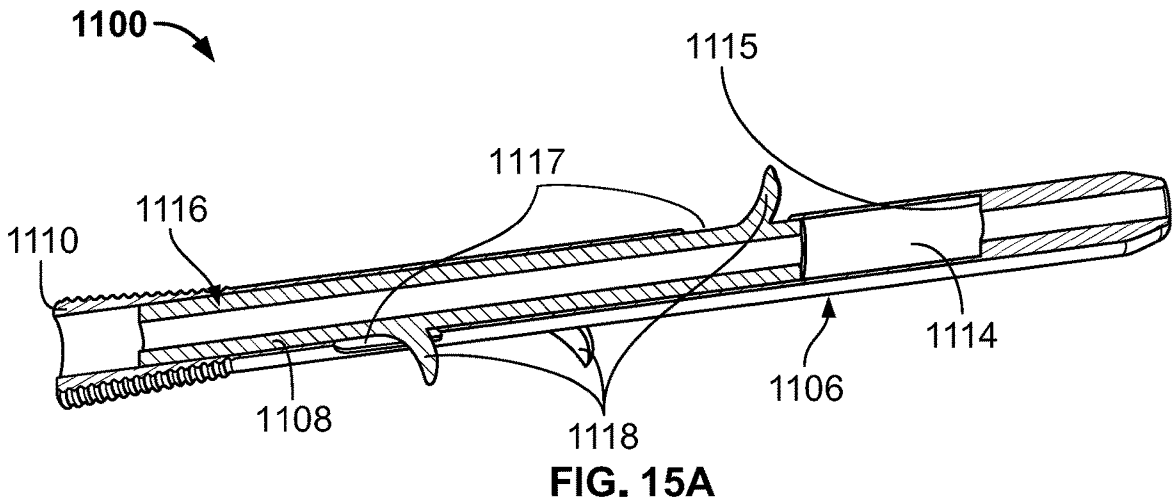
FIG. 15A is a cross-sectional view of a fracture fixation device according to another aspect of the present disclosure.

In a further alternative aspect, fingers 918, 1018 of fixation device 900, 1000 may be formed at different axial points along the length of anchoring member 916, 1016. For example, with reference to FIGS. 15A-15B, fracture fixation device 1100 includes collapsible and expandable anchoring member 1116 received within housing 1106. Upon distal movement of pin 1108, fingers 1118 extends through tracks 1117 to engage the surrounding bone surface. Housing 1106 defines a ledge 1115 to set a maximum distance anchoring member 1116 can be extended before a distal end of the anchoring member abuts against the ledge.

Figure 15B:
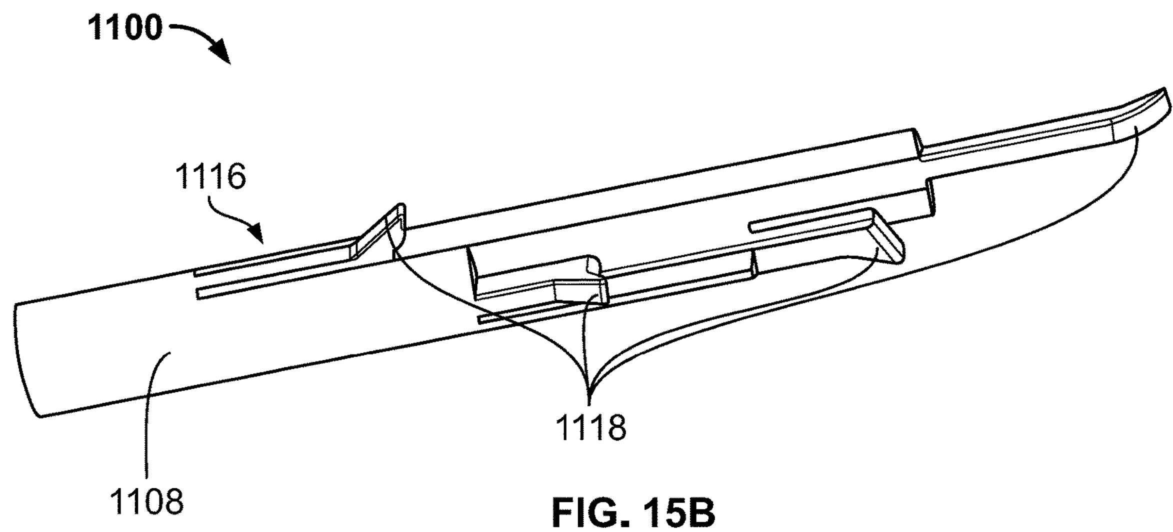
FIG. 15B is a perspective view of an anchoring member of the fracture fixation device of FIG. 15A.

As shown in FIG. 15B, fingers 1118 axially lies along different lengths of anchoring member 1116 such that fingers 1118 can engage the surrounding bone surface along a variety of points. This varied engagement allows for fixation device 1100 to be secured against the surrounding bone surface without relying on its engagement along a centralized location within the bone portion.

Figure 16A:
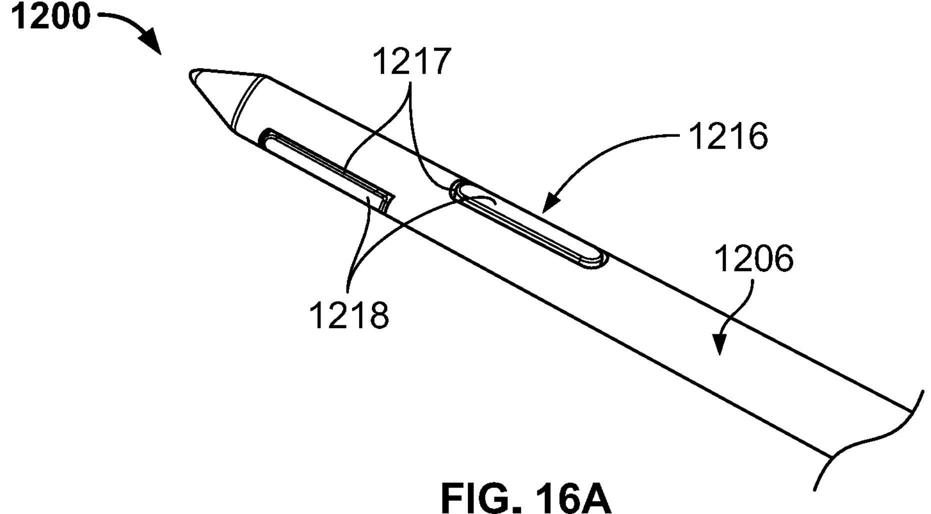
FIG. 16A is a partial view of a fracture fixation device according to another aspect of the present disclosure.
Figure 16B:
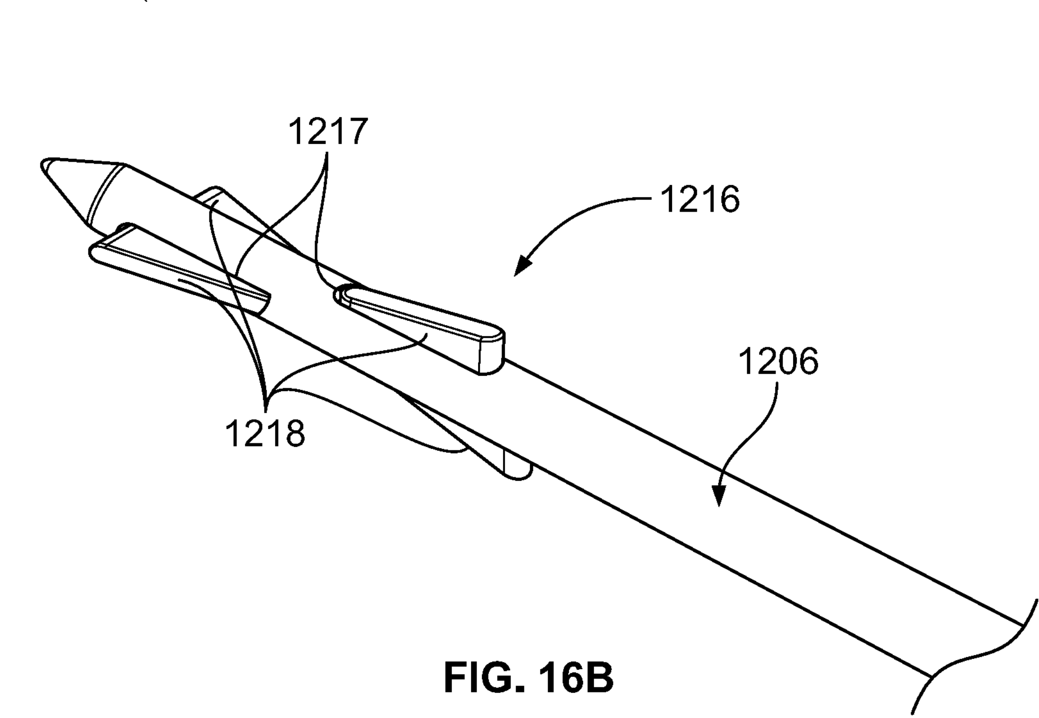
FIG. 16B is a perspective view of the fracture fixation device of FIG. 16A.

In a yet further alternative aspect, fingers 918, 1018, 1118 can are not curved, and can have an angular or wedge shape. For example, with reference to FIGS. 16A-16B, a collapsible and expandable anchoring member 1216 is inserted within housing 1206. In an unexpanded configuration, shown in FIG. 16A, wedges 1218 of anchoring member 1216 do not extend past tracks 1217 and lies substantially flush with an exterior surface of housing 1206. In an expanded configuration, an actuating tool (not shown) is inserted within anchoring member 1216 to expand wedges 1218 transversely through tracks 1217 to engage the surrounding bone surface. This can be done, for example, through a spring mechanism within anchoring member 1216 applying a force to wedges 1218 when actuated by the actuating tool.

With reference to FIGS. 13A-16B, the use of fixation device 900, 1000, 1100, 1200 is described. A surgeon first attaches bone plate 902 to proximal femur 10 by inserting cortical screws 904 through the openings 913 in superior wing 905 and inferior wing 907, and fastening the cortical screws into the femur as shown in FIG. 13A. The surgeon then compresses the plurality of fingers 918 toward the longitudinal axis of pin 908 to collapse anchoring member 916 in order to insert the distal end of pin 908 through the opening 919 of bone plate 902 and into the bore 914 of housing 906. As the surgeon advances pin 908 into the bore 914 of housing, compliant stopper 920 will compress as the stopper slides over the inwardly extending ledge 915 of housing 906. After stopper 920 has advanced over the ledge 915, the compliant stopper will expand and prevent pin 908 from backing out of housing 906.

With specific reference to fixation device 900, 1000, 1100, as pin 908, 1008, 1108 is advanced through the bore 914, 1014, 1114 of housing 906, 1006, 1106, the interior surface the sidewall of housing 906, 1006, 1106 prevents the plurality of fingers 918, 1018, 1118 from radially expanding, until the free ends of the arm members are positioned radially adjacent the entrance of tracks 917, 1017, 1117. Once the free ends of fingers 918 are positioned radially adjacent tracks 917, 1017, 1117, the fingers will expand in the radial direction and each one of the fingers will enter a respective track. Further axial advancement of pin 908, 1008, 1108 will force each one of the fingers to travel through its respective track. The arch shape of the track will aid the fingers in expanding radially. Once the fingers have extended completely through tracks 917, 1017, 1117, the fingers will engage cancellous bone to compress first bone portion 40 and second bone portion 42 and provide axial and rotational stability to the bone portions during healing of the fracture 38.

With specific reference to fixation device 1200, once anchoring member 1216 has been inserted within housing 1206, an actuation tool can be inserted within anchoring member 1216. Upon actuation of the actuating tool, wedges 1218 can expand exterior to housing 1206 to engage the surrounding bone area.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation device for stabilizing fractured bone portions comprising:

a housing having a proximal end, a distal end opposite the proximal end and a bore extending between the proximal and distal ends, the housing defining a longitudinal axis and a length from the proximal end to the distal end;

an actuator being at least partially disposed within the bore of the housing and selectively moveable through the bore, the actuator having expanding legs; and a first anchoring member coupled to the actuator and configured to transition between a first condition in which a portion of the first anchoring member has a first distance from the longitudinal axis and a second condition in which the portion of the first anchoring member has a second distance from the longitudinal axis, the second distance being greater than the first distance, wherein the housing maintains the length and is shaped to prevent the actuator from backing out of the housing upon expansion of the expanding legs.

2. The fixation device of claim 1, wherein the portion of the first anchoring member transitions from the first condition to the second condition to allow the portion of the first anchoring member to engage bone and assist in axially and rotationally securing the fractured bone portions.

3. The fixation device of claim 1, wherein the housing includes a protrusion which is configured to prevent the actuator from backing out of the housing.

4. The fixation device of claim 3, wherein the protrusion is a stopper extending radially inward from an inner surface of the housing.

5. The fixation device of claim 1, wherein the actuator is a compression screw.

6. The fixation device of claim 1, further comprising a wedge adapted to transition the first anchoring member from the first condition to the second condition.

7. The fixation device of claim 6, further comprising a second anchoring member coupled to the actuator and configured to transition between a first condition in which a portion of the second anchoring member has a first distance from the longitudinal axis and a second condition in which the portion of the second anchoring member has a second distance from the longitudinal axis, the second distance being greater than the first distance, wherein the wedge is adapted to transition the second anchoring member from the first condition to the second condition.

8. The fixation device of claim 7, wherein the wedge is conical and the first and second anchoring members are pivotal arms, and wherein the wedge is configured to engage the pivotal arms to force the pivotal arms to radially expand into surrounding bone.

9. A fixation device for stabilizing fractured bone portions comprising:

a housing having a proximal end, a distal end opposite the proximal end and a bore extending between the proximal and distal ends, the housing defining a longitudinal axis;

an actuator being at least partially disposed within the bore of the housing and moveable distally through the bore, the actuator having an expandable portion;

a first anchoring member coupled to the actuator and configured to transition between a first condition in which a portion of the first anchoring member has a first distance from the longitudinal axis and a second condition in which the portion of the first anchoring member has a second distance from the longitudinal axis, the second distance being greater than the first distance; and a wedge configured to be inserted axially into the housing to expand the expandable portion, wherein the expandable portion is configured to prevent the actuator from backing out of the housing upon expansion and the housing includes a ledge extending radially inward from an inner surface of the housing configured to engage the expandable portion to prevent proximal movement of the actuator, the ledge defining a gap therebetween spanning a first distance, wherein an outer diameter of the expandable portion in an expanded condition defines a second distance greater than the first distance.

10. The fixation device of claim 9, further comprising a wedge configured to actuate the expandable portion.

11. The fixation device of claim 10, wherein the wedge is conical in shape having a diameter which tapers in the axial direction.

12. The fixation device of claim 9, further comprising a second anchoring member coupled to the actuator and configured to transition between a first condition in which a portion of the second anchoring member has a first distance from the longitudinal axis and a second condition in which the portion of the second anchoring member has a second distance from the longitudinal axis, the second distance being greater than the first distance, the fixation device further comprising a wedge adapted to transition the first anchoring member from the first condition to the second condition and the second anchoring member from the first condition to the second condition.

13. The fixation device of claim 12, wherein the wedge is conical and the first and second anchoring members are pivotal arms, and wherein the wedge is configured to engage the pivotal arms to force the pivotal arms to radially expand into surrounding bone.

14. A fixation device for stabilizing fractured bone portions comprising:

a housing having a proximal end, a distal end opposite the proximal end and a bore extending between the proximal and distal ends, the housing defining a longitudinal axis;

an actuator being at least partially disposed within the bore of the housing and moveable distally through the bore, the actuator having an expandable portion;

a first anchoring member coupled to the actuator and configured to transition between a first condition in which a portion of the first anchoring member has a first distance from the longitudinal axis and a second condition in which the portion of the first anchoring member has a second distance from the longitudinal axis, the second distance being greater than the first distance; and a second anchoring member coupled to the actuator and configured to transition between a first condition in which a portion of the second anchoring member has a first distance from the longitudinal axis and a second condition in which the portion of the second anchoring member has a second distance from the longitudinal axis, the second distance being greater than the first distance, the fixation device further comprising a wedge adapted to transition the first anchoring member from the first condition to the second condition and the second anchoring member from the first condition to the second condition, wherein the expandable portion is configured to prevent the actuator from backing out of the housing upon expansion.

15. The fixation device of claim 14, wherein the wedge is conical and the first and second anchoring members are pivotal arms, and wherein the wedge is configured to engage the pivotal arms to force the pivotal arms to radially expand into surrounding bone.

* * * * *